(12) United States Patent
Kwon

(10) Patent No.: US 8,344,116 B2
(45) Date of Patent: Jan. 1, 2013

(54) POLYMERS AND COMPLEXES FOR DELIVERY OF NUCLEIC ACIDS TO INTRACELLULAR TARGETS

(75) Inventor: Young Jik Kwon, Irvine, CA (US)

(73) Assignee: Case Western Reserve University, Cleveland, OH (US)

( * ) Notice: Subject to any disclaimer, the term of this patent is extended or adjusted under 35 U.S.C. 154(b) by 599 days.

(21) Appl. No.: 12/405,313

(22) Filed: Mar. 17, 2009

(65) Prior Publication Data

US 2009/0233359 A1  Sep. 17, 2009

Related U.S. Application Data

(60) Provisional application No. 61/037,027, filed on Mar. 17, 2008.

(51) Int. Cl.
*C07H 21/02* (2006.01)
*C07H 21/04* (2006.01)
*C12N 15/11* (2006.01)
*A61K 48/00* (2006.01)

(52) U.S. Cl. .................... 536/23.1; 514/44 R; 514/44 A

(58) Field of Classification Search .......................... None
See application file for complete search history.

(56) References Cited

U.S. PATENT DOCUMENTS

| 6,077,663 | A | * | 6/2000 | Curiel et al. ...................... 435/5 |
| 6,846,809 | B2 | * | 1/2005 | Cristiano et al. ............. 514/44 R |
| 7,060,498 | B1 | * | 6/2006 | Wang ............................. 435/455 |
| 2004/0198687 | A1 | * | 10/2004 | Rozema et al. ................. 514/44 |
| 2005/0222064 | A1 | * | 10/2005 | Vargeese et al. ................ 514/44 |
| 2010/0009446 | A1 | * | 1/2010 | Poehlmann et al. .......... 435/375 |

OTHER PUBLICATIONS

In Kusumoto (2006) Cryotechnology, 51: 57-66.*
Arjen, et al. (2004) "Polymer Side-Chain Degradation as a Tool to Control the Destabilization of Polyplexes", Pharmaceutical Research, 21(1): 170-76.*
Khallil, et al. (2006) "Uptake Pathways and Subsequent Intracellular Trafficing in Nonviral Gene Delivery", Pharmacological Reviews, 58(1): 32-45.*

* cited by examiner

*Primary Examiner* — Robert M Kelly
(74) *Attorney, Agent, or Firm* — Tarolli, Sundheim, Covell & Tummino LLP

(57) ABSTRACT

A complex includes a nucleic acid and a cationic polymer with at least one side chain coupled to the nucleic acid. The at least one side chain including an acid degradable amine-bearing ketal or acetal linkage.

17 Claims, 11 Drawing Sheets

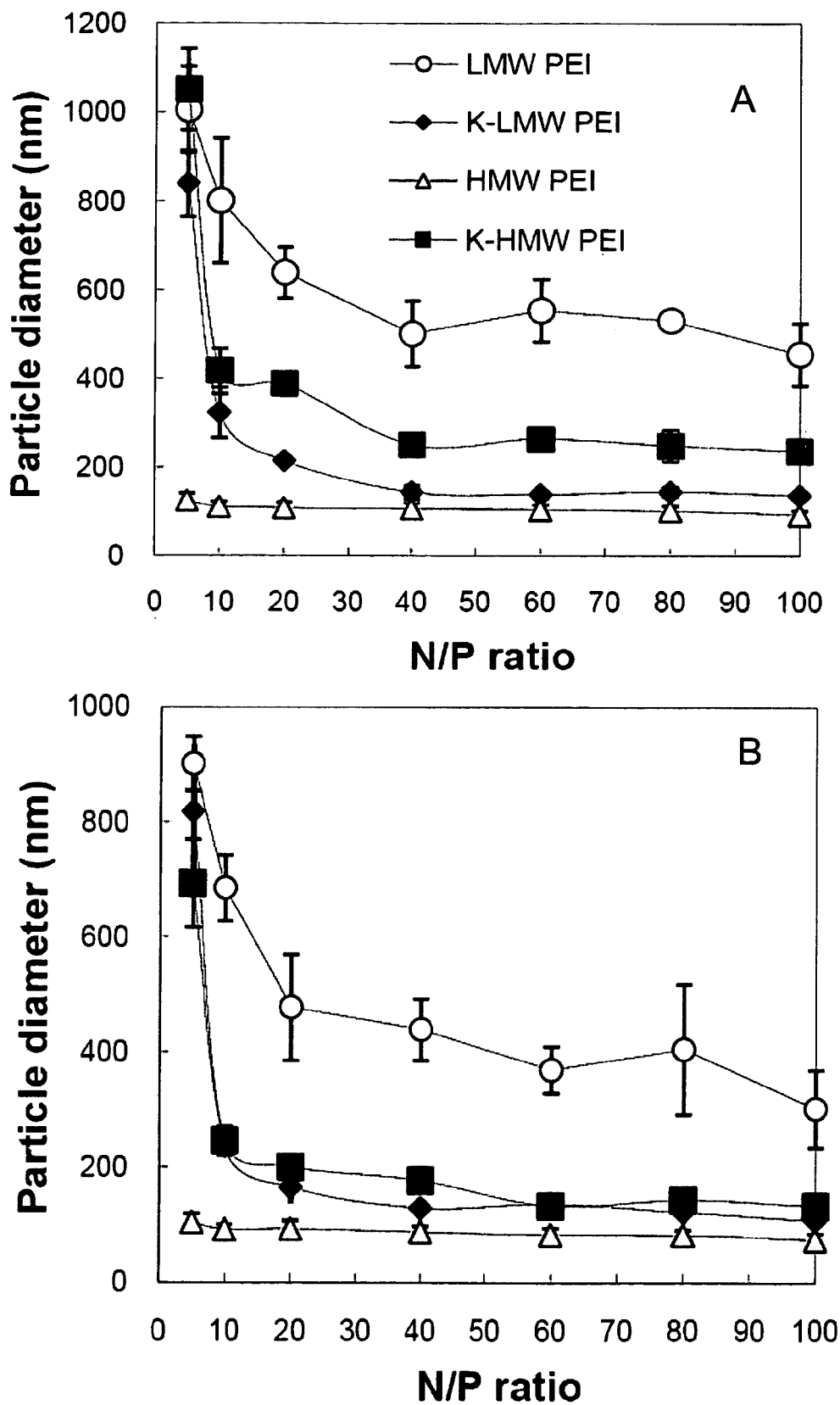
Fig. 5A-B

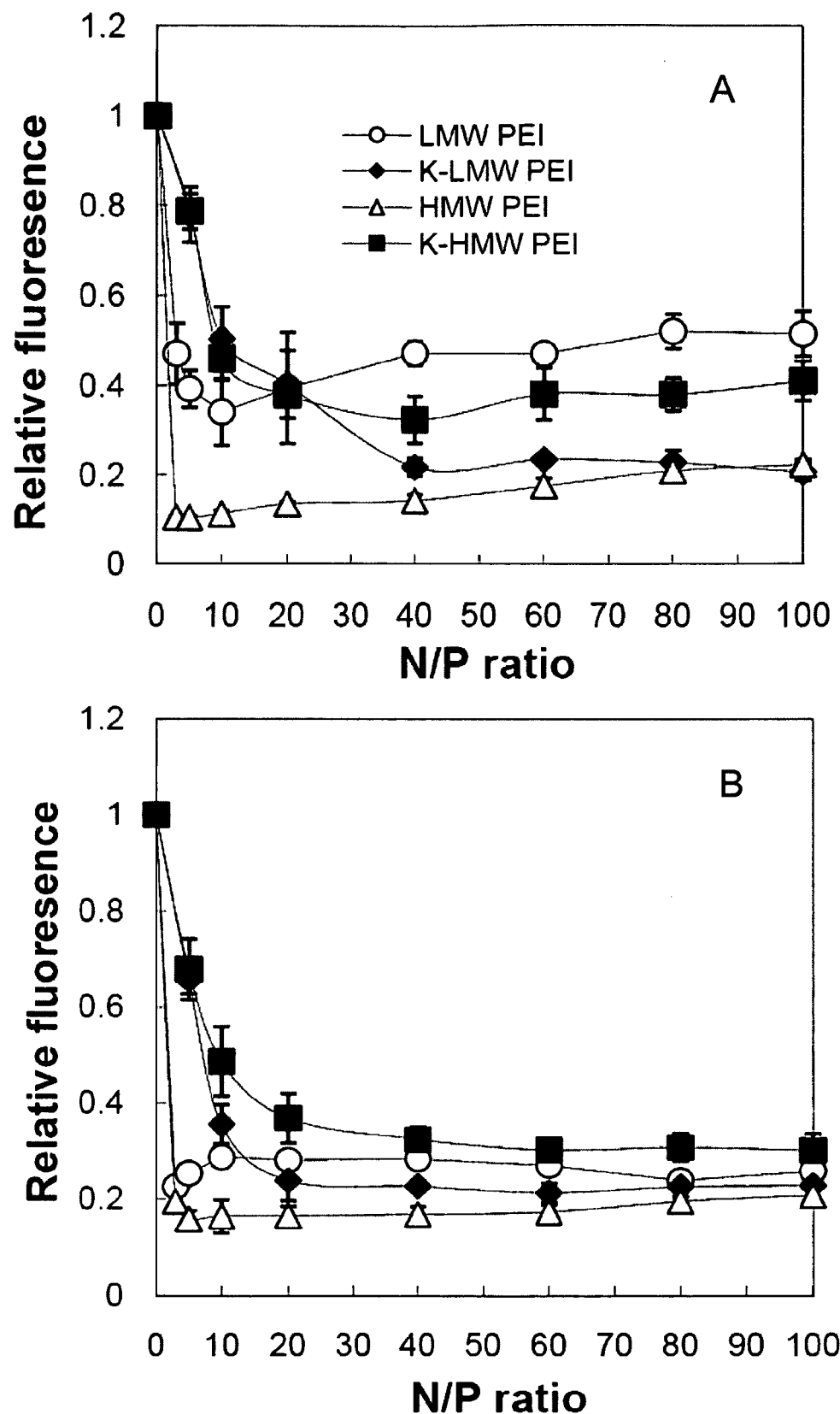
Fig. 6A-B

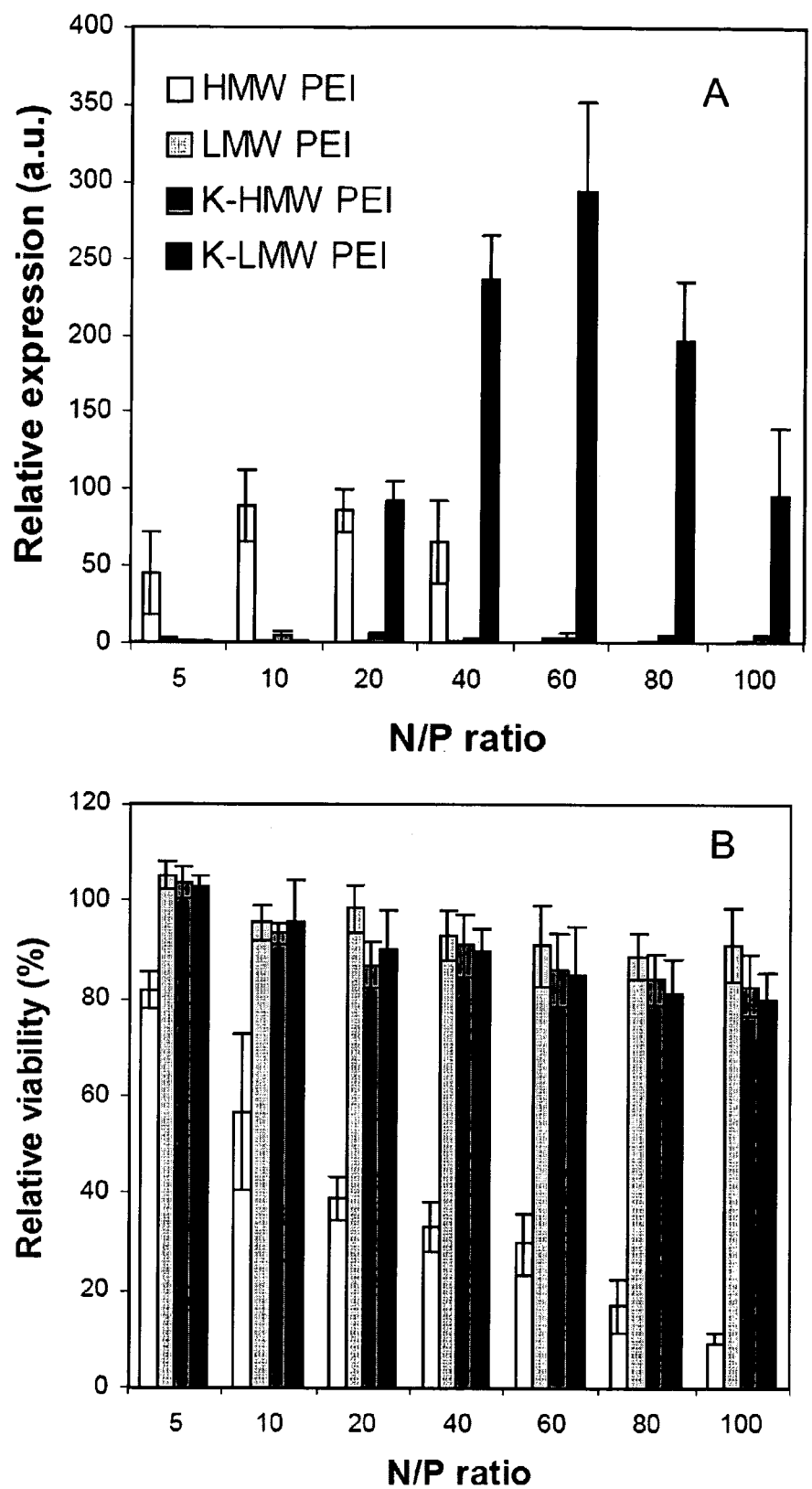
Fig. 7A-B

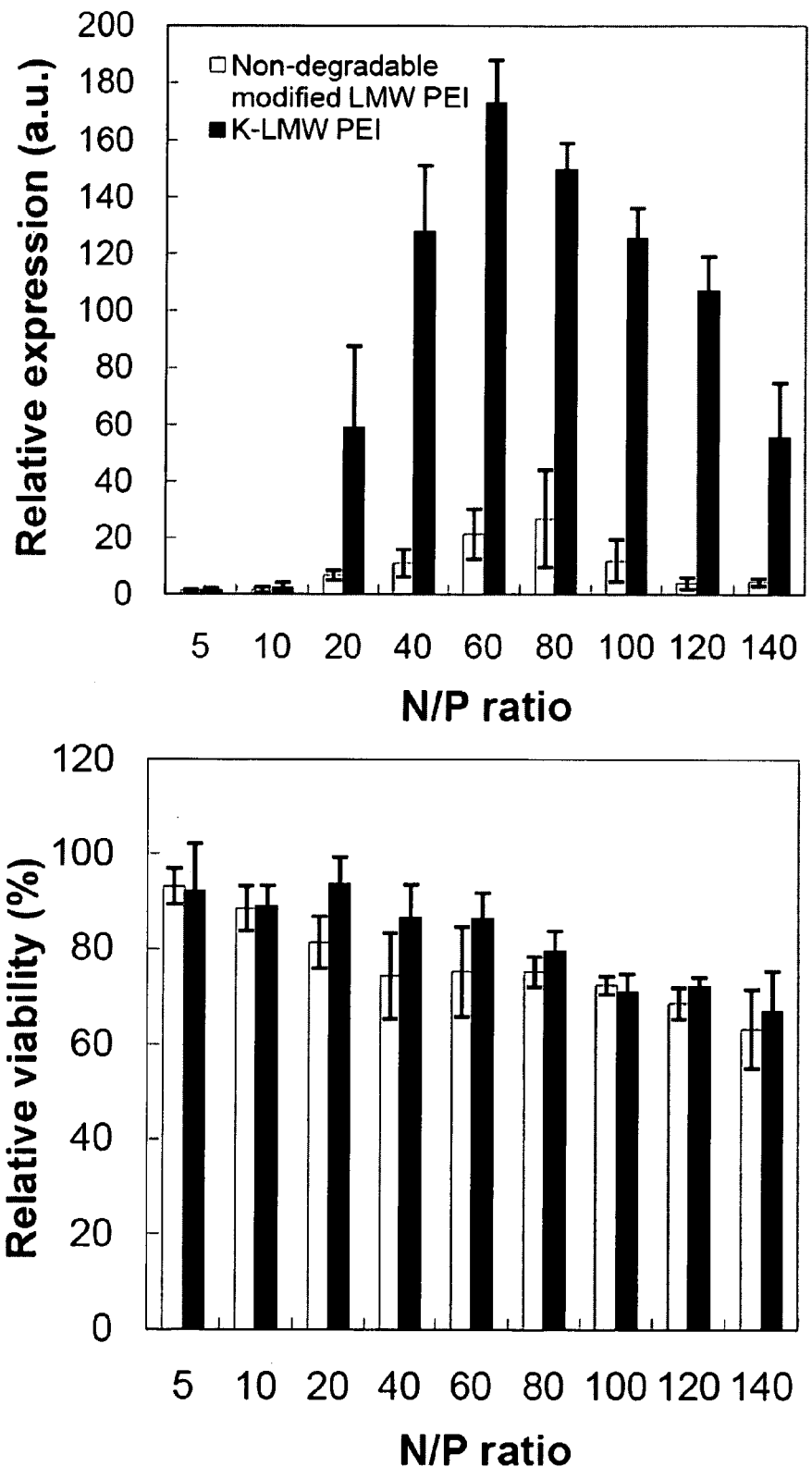
Fig. 8A-B

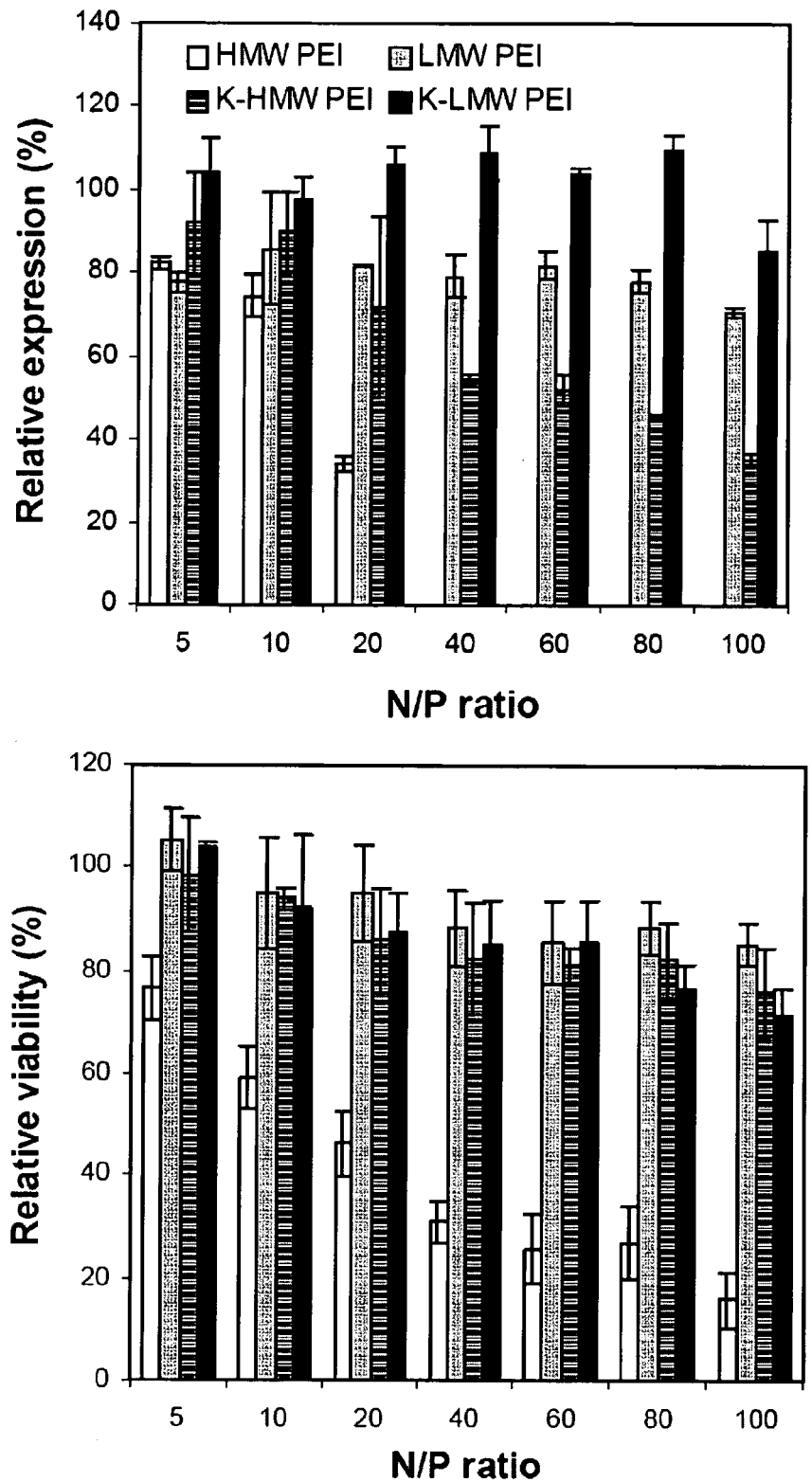
Fig. 9A-B

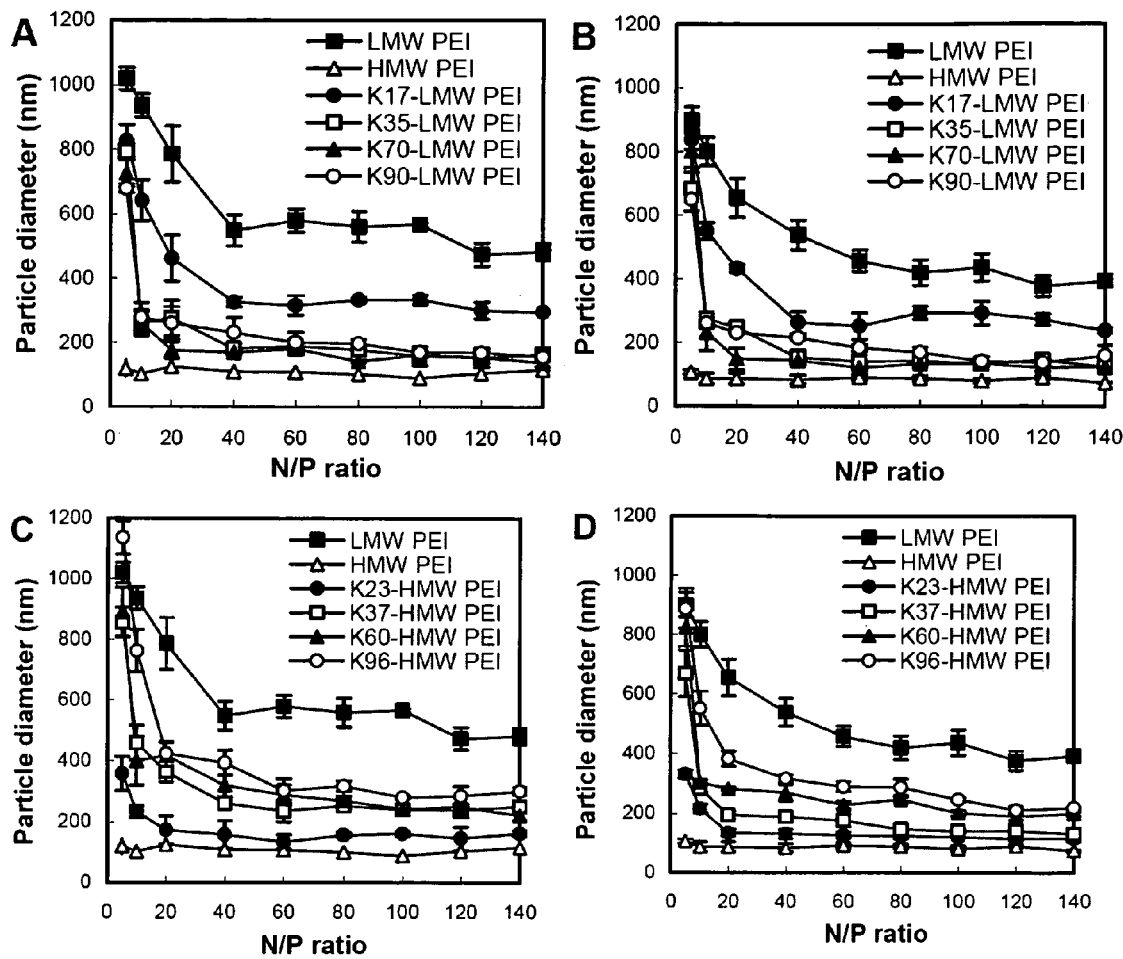
Fig. 10A-D

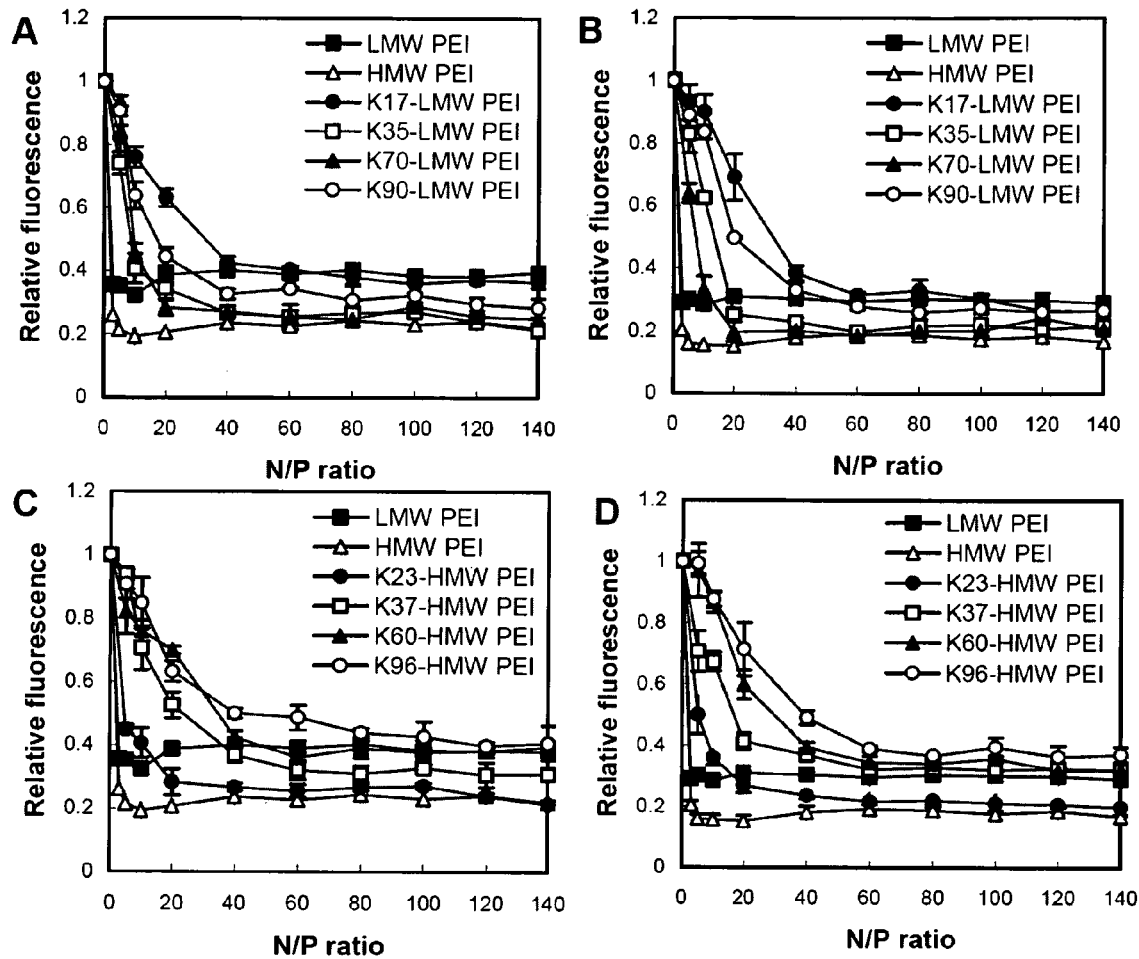
Fig. 11A-D

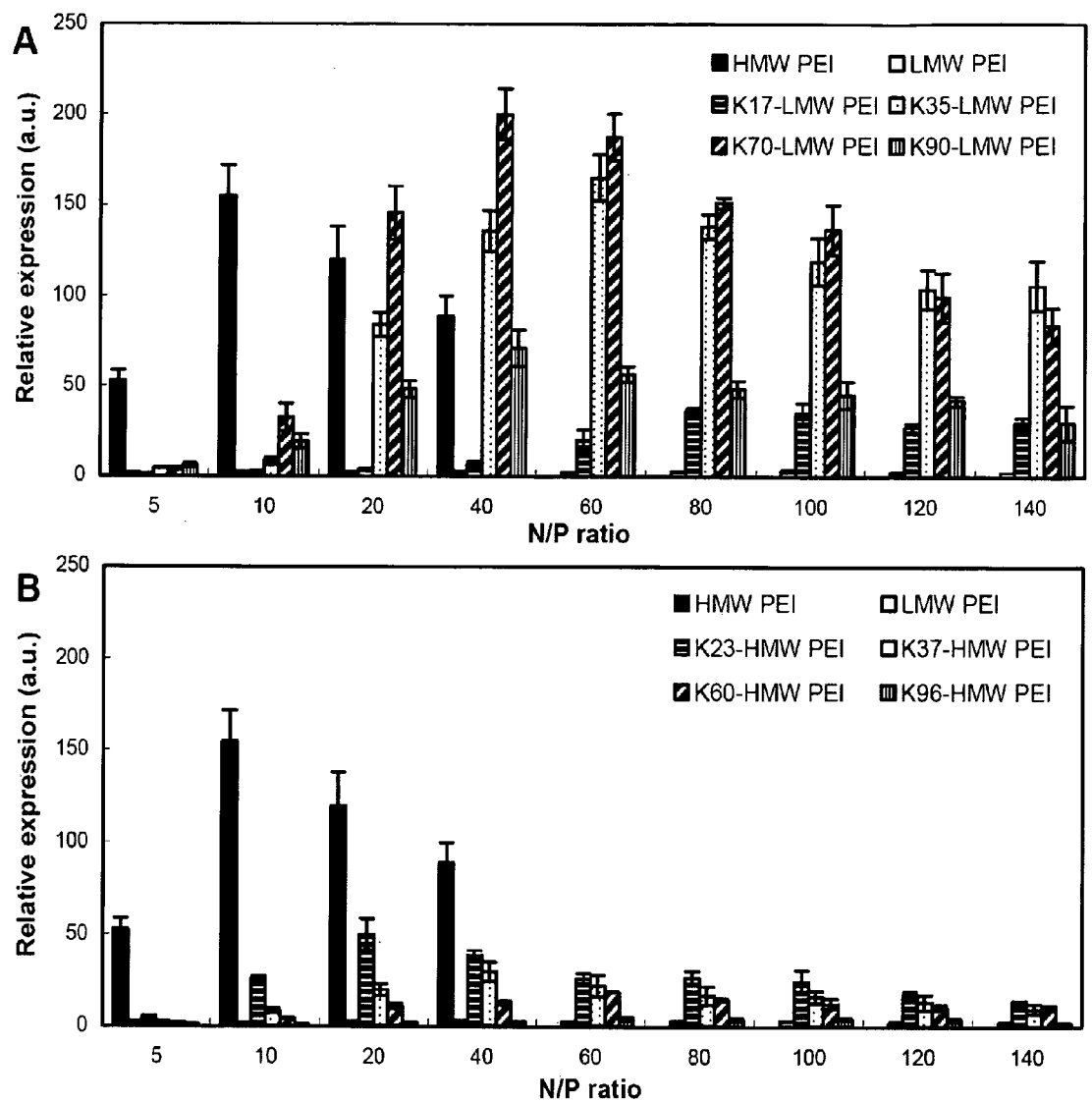
Fig. 12A-B

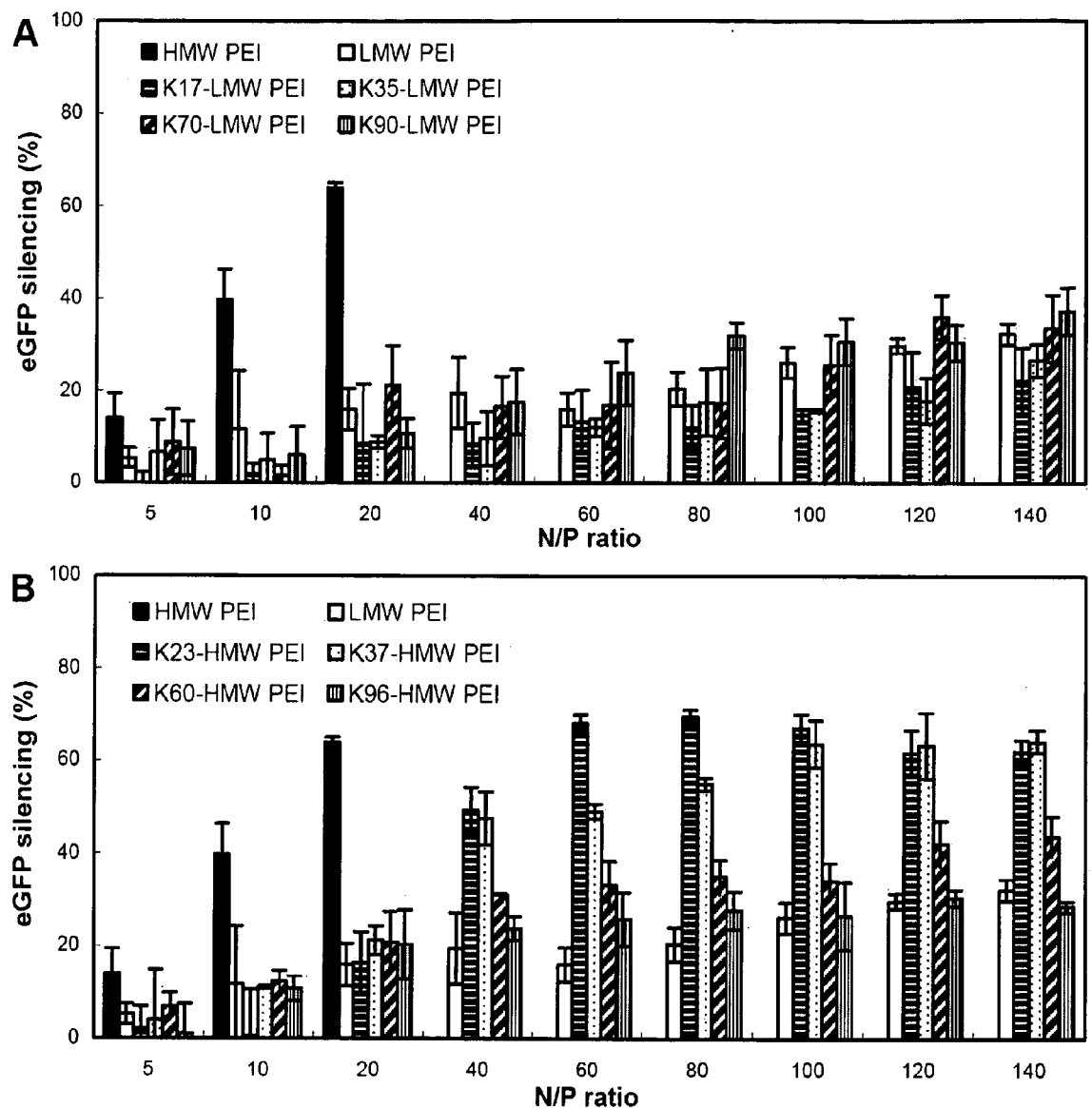
Fig. 13A-B

POLYMERS AND COMPLEXES FOR DELIVERY OF NUCLEIC ACIDS TO INTRACELLULAR TARGETS

RELATED APPLICATION

This application claims priority from U.S. Provisional Application No. 61/037,027, filed Mar. 17, 2008, the subject matter, which is incorporated herein by reference.

FIELD OF THE INVENTION

The present invention relates to acid degradable polymers and complexes for delivery of nucleic acids to intracellular targets and methods of using a ketalized or acetalized polymers for the delivery of nucleic acids to an intracellular target.

BACKGROUND

Gene delivery systems can be divided into viral and non-viral systems. Non-viral gene delivery systems, based on "naked DNA" or formulated plasmid DNA, have potential benefits over viral vectors due to simplicity of use and lack of inciting a specific immune response. A number of synthetic gene delivery systems have been described to overcome the limitations of naked DNA, including cationic lipids, peptides, and polymers.

Polymers, on the other hand, have emerged as a viable alternative to current systems because of their excellent molecular flexibility allows for complex modifications and incorporation of novel chemistries. Cationic polymers, such as poly(L-lysine) (PLL) and poly(L-arginine) (PLA), polyethyleneimine (PEI) have been widely studied as gene delivery candidates due to their ability to condense DNA, and promote DNA stability and transmembrane delivery. The transfection efficiency of the cationic polymers is influenced by their molecular weight. Polymers of high molecular weight, e.g., greater than 20 kD, have better transfection efficiency than polymers of lower molecular weight. Polymers with high molecular weights, however, are more cytotoxic.

Poly(ethyleneimine) (PEI) condenses DNA into small narrowly distributed positively charged spherical complexes and can transfect cells in vitro and in vivo. PEI is similar to other cationic polymers in that the transfection activity of PEI increases with increasing polymer/DNA ratios. Commercial branched PEI is composed of 25% primary amines, 50% secondary amines and 25% tertiary amines.

SUMMARY OF THE INVENTION

The present invention relates to a complex that comprises a nucleic acid and a cationic polymer with at least one side chain that couples the nucleic acid to the cationic polymer. The at least one side chain includes an acid degradable amine-bearing ketal or acetal linkage. In an aspect of the invention, the cationic polymer is a polyamine, for example, a polyethyleneimine.

In another aspect of the invention, the at least one side chain can include a ketal group or acetal group having the following general formula:

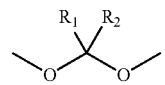

wherein $R_1$ and $R_2$ are each individually selected from the group consisting of H, an alkyl, and a substituted alkyl.

In a further aspect, the at least one side chain can have the following general formula:

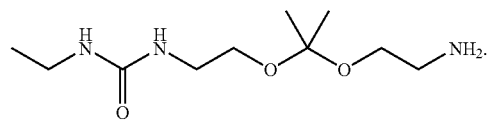

In yet another aspect, the polyethyleneimine can have a molecular weight of about 400 to about 1200 daltons and the nucleic acid can comprise DNA. The polyethyleneimine can also have a molecular weight of about 20 to about 30 kilodaltons and the nucleic acid can comprise at least one of siRNA or microRNA. The molar ratio of nitrogen atoms in the polyethyleneimine to phosphate atoms in the nucleic acid (N/P ratio) can be about 25 to about 100, for example, about 40 to about 80. The ketalization ratio of the complex can be about 35% to about 70%.

The present invention also relates to a complex that comprises a nucleic acid and a polyethyleneimine coupled to the nucleic acid. The polyethyleneimine can include a repeating unit with the following general formula:

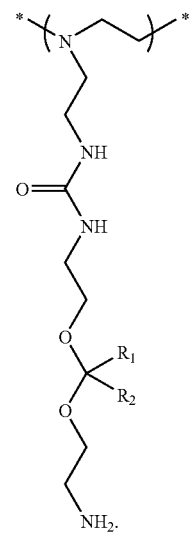

In yet another aspect, the polyethyleneimine can have a molecular weight of about 400 to about 1200 daltons and the nucleic acid can comprise DNA. The polyethyleneimine can also have a molecular weight of about 20 to about 30 kilodaltons and the nucleic acid can comprise at least one of siRNA or microRNA. The molar ratio of nitrogen atoms in the polyethyleneimine to phosphate atoms in the nucleic acid (N/P ratio) can be about 25 to about 100 and more specifically about 40 to about 80. The ketalization ratio of the complex can be about 35% to about 70%.

The present invention also relates to a method of affecting a cell. The method includes administering to the cell a first complex and a second complex. The first complex includes RNA and a polyethyleneimine having a molecular weight of about 20 to about 30 kilodaltons with at least one side chain that is coupled to the RNA. The at least one side chain includes an acid degradable amine-bearing ketal or acetal linkage. The second complex includes DNA and a polyethyleneimine having a molecular weight of about 400 to about 1200 daltons with at least one side chain that is coupled to the DNA. The at least one side chain can include an acid degradable amine-bearing ketal or acetal linkage. The first complex and the second complex can be administered to the cell sequentially or the first complex and the second complex can be administered to the cell substantially simultaneously.

The present invention also relates to a pharmaceutical composition that comprises at least one of a first complex or a second complex. The first complex includes RNA and a polyethyleneimine having a molecular weight of about 20 to about 30 kilodaltons with at least one side chain that is coupled to the RNA. The at least one side chain includes an acid degradable amine-bearing ketal or acetal linkage. The second complex includes DNA and a polyethyleneimine having a molecular weight of about 400 to about 1200 daltons with at least one side chain that is coupled to the DNA. The at least one side chain can include an acid degradable amine-bearing ketal or acetal linkage. In an aspect of the invention, the pharmaceutical composition can include the first complex and the second complex.

The present invention further relates to a branched polyethyleneimine including a repeating unit with the following general formula:

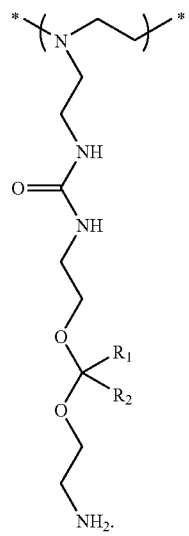

BRIEF DESCRIPTION OF THE DRAWINGS

FIG. 5 illustrates plots showing particle size of (A) DNA/PEI and (B) siRNA/PEI polyplexes at various N/P ratios, determined by DLS analysis.

FIG. 6 illustrates plots showing nucleic acid condensation efficiency of (A) DNA/PEI and (B) siRNA/PEI polyplexes at various N/P ratios, measured by ethidium bromide exclusion assay.

FIG. 7 illustrates tables showing (A) transfection activity and (B) cytotoxicity evaluation of the various PEI/nucleic acids polyplexes at various N/P ratios. Notice that there were an insufficient number of live cells to analyze for gene expression after being incubated with HMW PEI at N/P ratio of 40 and above (A).

FIG. 8 illustrates tables showing (A) evaluation of the effect of acid-degradable ketalization of PEI on DNA transfection activity. (B) Cytotoxicity evaluation of acid-degradable ketalized PEI and nondegradable modified LMW PEI at various N/P ratios. Unmodified LMW PEI polyplexes showed immeasurable transfection with the similar cytotoxicity to K-LMW PEI polyplexes.

FIG. 9 illustrates tables showing (A) siRNA interference activity and (B) cytotoxicity evaluation of the various PEI/nucleic acid polyplexes at various N/P ratios.

FIG. 10 illustrates plots showing particle size of (A) pDNA/K-LMW PEI, (B) siRNA/K-LMW PEI, (C) pDNA/K-HMW PEI, and (D) siRNA/K-HMW PEI polyplexes at various ketalization ratios and N/P ratios, determined by DLS analysis. Note that particle size of nucleic acids/HMW PEI (25 kDa) and nucleic acids/LMW PEI (0.8 kDa) polyplexes were measured as a control.

FIG. 11 illustrates plots showing nucleic acid complexation efficiency of (A) pDNA/K-LMW PEI, (B) siRNA/K-LMW PEI, (C) pDNA/K-HMW PEI, and (D) siRNA/K-HMW PEI polyplexes at various ketalization ratios and N/P ratios, measured by ethidium bromide exclusion assay.

FIG. 12 illustrates tables showing transfection efficiency of pDNA/PEI polyplexes at various ketalization ratios and N/P ratios. (A) GFP expression in NIH 3T3 cells transfected by (A) pDNA/K-LMW PEI and (B) pDNA/K-HMW PEI polyplexes. Notice that there were an insufficient number of live cells to analyze for gene expression after being incubated with HMW PEI at N/P ratio of 60 and above (A and B).

FIG. 13 illustrates tables showing eGFP gene silencing efficiency of siRNA/PEI polyplexes at various ketalization ratios and N/P ratios. eGFP knockdown in NIH 3T3 cells by (A) siRNA/K-LMW PEI and (B) siRNA/K-HMW PEI polyplexes. Notice that there were an insufficient number of live cells to analyze for gene silencing after being incubated with HMWPEI at N/P ratio of 40 and above (A and B).

DETAILED DESCRIPTION

Figure 1:
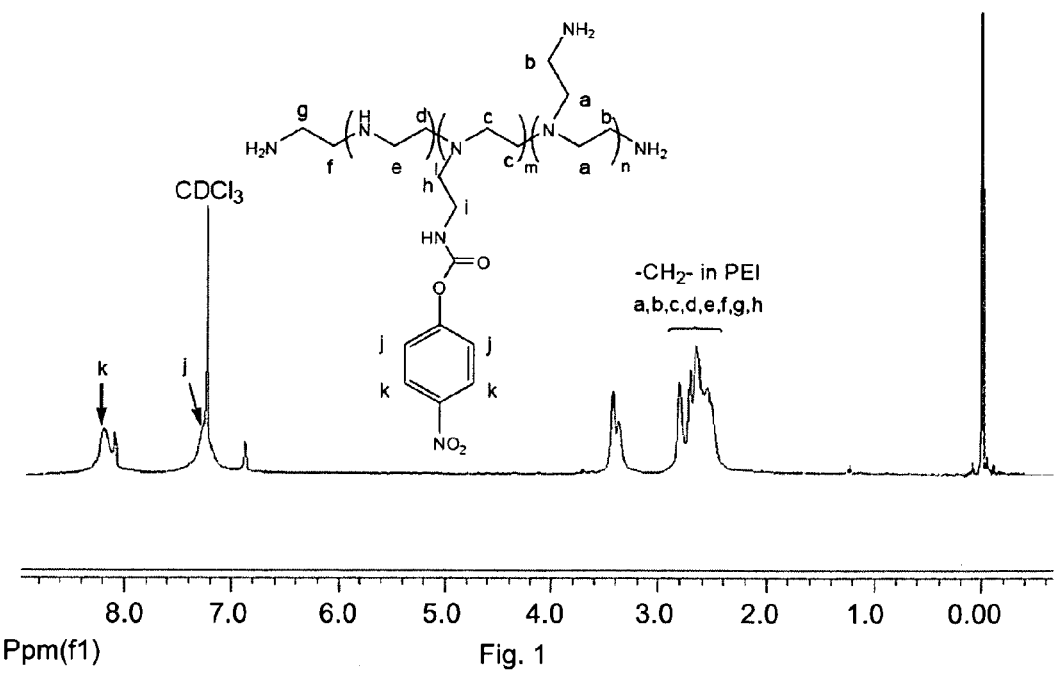
FIG. 1 illustrates 1H-NMR spectrum of p-nitrophenyl carbamate-activated LMW PEI.

Methods involving conventional molecular biology techniques are described herein. Such techniques are generally known in the art and are described in detail in methodology treatises, such as Current Protocols in Molecular Biology, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., Glossary of Genetics: Classical and Molecular, 5th Edition, Springer-Verlag: New York, 1991, and Lewin, Genes V, Oxford University Press: New York, 1994. The definitions provided herein are to facilitate understanding of certain terms used frequently herein and are not meant to limit the scope of the present invention.

In the context of the present invention, the term "ketal" refers to a functional group bearing two alkyl groups and two alkoxy groups on one carbon atom. Ketals typically have the formula R2C(OR)2 and are produced in the acid-catalyzed alcoholysis of a ketone or a hemiketal.

As used herein, the term "acetal" refers to a functional group bearing an alkyl group, a hydrogen atom, and two alkoxy groups on one carbon atom. Acetals typically have the formula RCH(OR)2 and are produced in the acid-catalyzed alcoholysis of an aldehyde or a hemiacetal.

As used herein, the terms "alkyl" or "substituted alkyl" refer to a straight chain or branched chain hydrocarbon radical having from about 1 to about 10 carbon atoms. Examples of such alkyls or substituted alkyls include methyl, ethyl, n-propyl, isopropyl, n-butyl, isobutyl, s-butyl, t-butyl, pentyl, neopentyl, hexyl, isohexyl, and the like.

The present invention relates to cationic polymers that include at least one side chain, which has an acid degradable amine-bearing ketal (or acetal) linkage. The at least one side chain can couple with a nucleic acid to form a cationic polymer-nucleic acid complex. The cationic polymer nucleic acid complex can be used to introduce the nucleic acid into a cell for purposes, such as RNA interference and/or transfection of the cell.

Upon delivery of the complexes to the cell, hydrolysis of the ketal (or acetal) linkages of the polymers contributes to endosomal disruption simultaneously with proton sponge effect. Upon degradation of the ketal or acetal linkages, nucleic acids provided in complexes with the polymers are efficiently released from cationic polymer backbone in the cell. Moreover, hydroxyl arms of ketalized polymer after hydrolysis may associate with endogenous DNA in the cell with weaker interactions than amine groups of un-ketalized polymers, reducing the possibility of generating undesirable side-effects.

In an aspect of the invention, the cationic polymer is a polyamine, such as a polyethyleneimine. The polyethyleneimine can include the following repeating unit

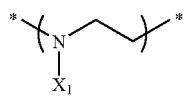

where $X_1$ is the side chain that includes the acid degradable amine-bearing ketal or acetal linkage. In an aspect of the invention, the side chain can include a primary amine that can couple the side chain with the nucleic acid.

The acetal or ketal linkage of the side chain can include an acetal or ketal group having the following formula:

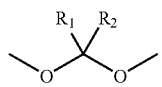

where $R_1$ and $R_2$ are each individually selected from the group consisting of H, an alkyl, and a substituted alkyl. The acetal or ketal group readily hydrolyzes in the acidic cytoplasm (e.g., about pH 5.0) of the cell and cleaves to form hydroxyls. By way of example, the side chain can have the following formula:

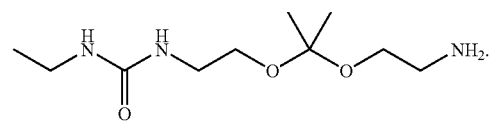 [SMILES: CCNC(=O)NCCOC(C)(C)OCCN]

The side chain can extend from a nitrogen atom of the polyethyleneimine as shown below.

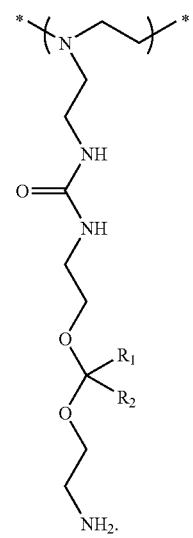

In an aspect of the invention the polymer used to form a complex with the nucleic acid can have the following formula:

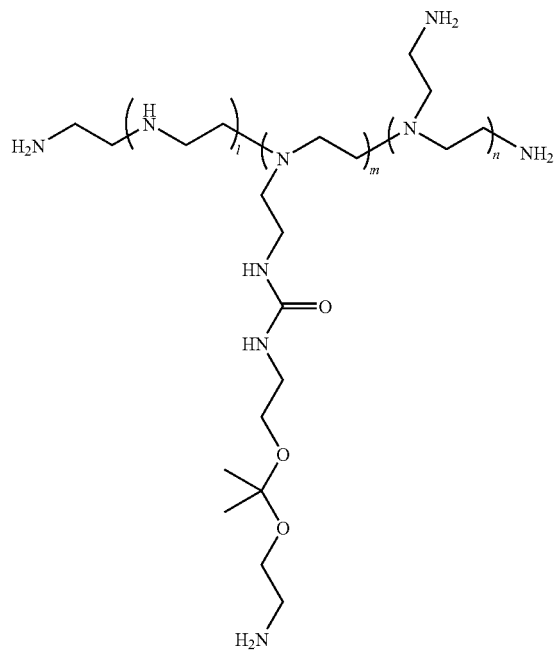

where l, m, and n can be at least about 1 and be block structures or be randomly distributed in the polymer. In one aspect, l, m, and n are at least 1 and randomly distributed in the polymer.

The polyethyleneimine with the acid degradable amine-bearing ketal (or acetal) linkage can be prepared by conjugating primary amines, such as branched primary amines, of low molecular weight and/or high molecular weight with an acid degradable amine-bearing ketal linkage. The low molecular weight polyethyleneimine can have a molecular weight of about 400 to about 1200 daltons (e.g., about 800 daltons) and the high molecular weight polyethyleneimine can have a molecular weight of about 20 to about 30 kilodaltons (e.g., about 25 kDa). The ketalization ratio of the complex can be about 35% to about 70%.

In an aspect of the invention, the nucleic acid used to form the complex with the polymer can be, for example, DNA or RNA. The nucleic acid can be an oligonucleotide or a nucleic acid construct. The nucleic acid can also comprise DNA that encodes one or more genes. For example, the nucleic acid can be plasmid DNA.

In one example, the nucleic acid may comprise a nucleotide sequence which codes for a pharmacological active substance or its precursor and/or which codes for an enzyme. The nucleic acid may also comprise a nucleotide sequence, which codes for an antigen of a pathogen. Pathogens and relevant antigens belonging thereto are, for example: herpes simplex virus
(HSV-1, HSV-2) and glycoprotein D; human immunodeficiency virus (HIV) and Gag, Nef, Pol; hepatitis C virus and NS3; anthrax and lethal factor, leishmania and ImSTI1 and TSA; tuberculosis bacteria and Mtb 8.4. It is possible in principle to employ any nucleic acid which codes for an antigen against which there is an immune response. Diverse nucleic acids coding for antigens can be combined if necessary.

In another example, the nucleic acid may comprise a nucleotide sequence which codes for an immunomodulatory protein, such as cytokines (for example IL-4, IFNγ,
IL-10, TNFα), chemokines (for example MCP-1, MIP1α, RANTES), costimulators (for example CD80, CD86, CD40, CD40L) or others (for example heat shock protein). The nucleic acid may, where appropriate, comprise a nucleotide sequence which codes for a fusion protein. The nucleic acid also comprises sequences which lead to a particular gene being expressed specifically, for example virus-specifically (that is to say, for example, only in virus-infected cells), (target) cell-specifically, metabolically specifically, cell cycle-specifically, development-specifically or else nonspecifically.

In another example, the nucleic can comprise small RNA (e.g., about 10 to about 100 bases) that are capable of inhibiting expression of at least one mRNA in a cell. The small RNA can be, for example, siRNA or microRNA (i.e., miRNA). SiRNA is typically synthesized from endogenous or exogenous double-stranded RNA (dsRNA) molecules having hairpin structures and processed such that numerous siRNA molecules are produced from both strands of the hairpin. In contrast, miRNA molecules are typically produced from endogenous dsRNA molecules having one or more hairpin structure such that a single miRNA molecule is produced from each hairpin structure. The terms "siRNA" and "miRNA" are intended to be consistent with their use in the art as described, for example, in Ambros et al., RNA 9:277-279 (2003).

The molar ratio of nitrogen atoms in the polyethyleneimine to phosphate atoms in the nucleic acid (N/P ratio) can be about 25 to about 100. Alternatively, the molar ratio of nitrogen atoms in the polyethyleneimine to phosphate atoms in the nucleic acid (N/P ratio) can be about 40 to about 80.

In an aspect of the invention, a low molecular weight polyethyleneimine (e.g., about 400 to about 1200 daltons) with at least one side chain including acid degradable amine-bearing ketal linkage (i.e., ketalized low molecular weight polyethyleneimine) can be provided in a complex with plasmid DNA. It was found that the ketalized low molecular weight polyethyleneimine has a high transfection efficiency and can readily transport plasmid DNA to the cell nucleus with minimal cytoxicity.

In another aspect of the invention, a high molecular weight polyethyleneimine (e.g., about 20 to about 30 kilodaltons) with at least one side chain including acid degradable amine-bearing ketal linkage (i.e., ketalized high molecular weight polyethyleneimine) can be provided in a complex with siRNA. It was found that the ketalized high molecular weight polyethyleneimine can be an efficient carrier of siRNA interfering mRNA in the cytoplasm of a cell.

The present invention further relates to the use of the complexes according to the invention. For example, the complexes can be used to introduce a nucleic acid into a cell or target cell (transfection), to produce a pharmaceutical and/or in gene therapy, and prophylactic and therapeutic vaccination and tolerance induction in the case of allergies. The invention can relate to the use of the complexes according to the invention for introducing nonviral or viral nucleic acid constructs into a cell and to the administration of this (transfected) cell to a patient for the purpose of prophylaxis or therapy of a disease. The cell can be, for example, an endothelial cell, a lymphocyte, a macrophage, a liver cell, a fibroblast, a muscle cell or an epithelial cell, and be applied locally onto the skin or injected subcutaneously, intramuscularly, into a wound, into a body cavity, into an organ or into a blood vessel. In another aspect, the invention relates to the use of the complexes according to the invention for the prophylaxis or therapy of a disease. The complexes according to the invention can be administered to the subject in a conventional way, for example, orally, parenterally or topically. By way of example, the complexes according to the invention can be given or injected perlingually, intranasally, dermally, subcutaneously, intravenously, intramuscularly, rectally, into a wound, into a body cavity, into a body orifice, into an organ or into a blood vessel.

It may be worthwhile where appropriate to combine the complexes according to the invention with further additions (adjuvants, anesthetic etc.).

The present invention further relates to a process for producing a transfected cell or target cell, where the complexes according to the invention are incubated with this cell. The transfection can be carried out in vitro. The invention further relates to a transfected cell or target cell which contains the complexes according to the invention. The invention further relates to the use of the transfected cell, for example as pharmaceutical or for producing a pharmaceutical and/or for gene therapy.

The present invention further relates to a pharmaceutical composition, which contains the complexes according to the invention and/or a cell transfected therewith. In an aspect of the invention, the pharmaceutical composition can include at least one of a first complex or a second complex. The first complex includes RNA and a polyethyleneimine having a molecular weight of about 20 to about 30 kilodaltons with at least one side chain. The at least one side chain includes an acid degradable amine-bearing ketal or acetal linkage. The second complex includes DNA and a polyethyleneimine having a molecular weight of about 400 to about 1200 daltons with at least one side chain. The at least one side chain including an acid degradable amine-bearing ketal or acetal linkage. In an aspect of the invention, the pharmaceutical composition can include the first complex and the second complex.

The present invention also relates to the coupling of the polymers according to the invention to a cell-specific ligand and to the use of the coupling product in a complex with a viral or nonviral nucleic acid for introducing this nucleic acid into a cell or for administering the complex to a mammal for the prophylaxis or therapy of a disease. The possibilities for producing and coupling cell-specific ligands has already been described in detail in the patent applications EP-A 0 790 312 and DE-A 196 49 645, which are incorporated by reference in their entirety.

The present invention also relates to cells, in particular from yeasts or mammals, into which a nucleic acid construct has been introduced with the aid of the complexes according to the invention. In one embodiment, the nucleic acid constructs are introduced with the aid of the complexes according to the invention into cell lines that can then be used after transfection for expression of the chosen gene. These cells can thus be used to provide a pharmaceutical for patients.

The invention further relates to the use of mammalian cells into which a nucleic acid has been introduced with the aid of the complexes according to the invention for producing a pharmaceutical for the treatment or prophylaxis of a disease. For example, endothelial cells can be obtained from the blood, be treated in vitro with the complexes according to the invention and be injected, for example intravenously, into the patient. A further possibility is, for example, for dendritic cells (antigen-presenting cells) to be obtained from blood, be treated in vitro with the complexes according to the invention and be injected into the patient to induce a prophylactic or therapeutic immune response. Such cells transfected in vitro can also be administered to patients in combination with the complexes according to the invention. This combination comprises cells and complexes being administered or injected in each case simultaneously or at different times, at the same or at different sites.

The following Examples are for the purpose of illustration and are not intended to limit the scope of the claims, which are appended hereto.

EXAMPLE 1

Controlled Delivery of Plasmid DNA and siRNA to Intracellular Targets using Ketalized Polyethyleneimine We modified low molecular weight (LMW, 800 Da) and high molecular weight (HMW, 25 kDa) PEI to accomplish enhanced and controlled delivery of plasmid DNA and siRNA to the nucleus and cytoplasm, respectively, through reduced cytotoxicity and enhanced dissociation of the nucleic acids from the polymers as shown in scheme 1.

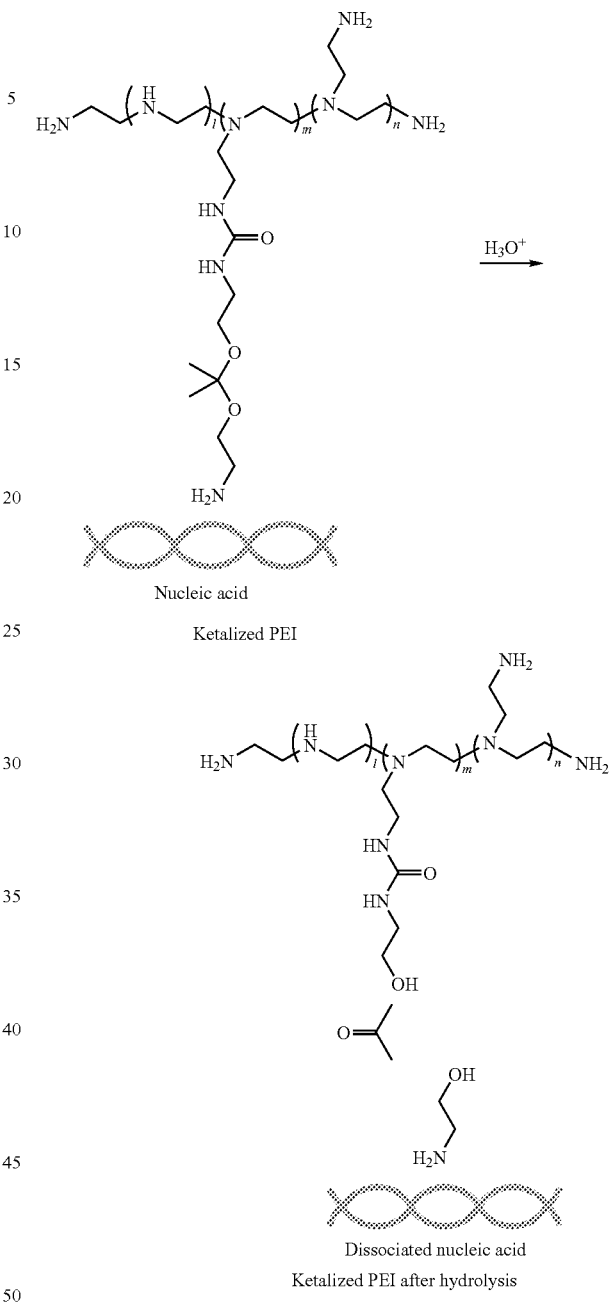

Primary amines of branched LMW and HMW PEI were partially conjugated with acid-degradable amine-bearing ketals. Ketal linkages are highly labile at mild acidic pHs (e.g., pH 5.0) and facilitate release of DNA and proteins from the acidic endosome and lysosome into the cytoplasm. As a result, these pH-sensitive biodegradable linkages have been employed for cytoplasmic delivery and drug delivery carriers. Condensation and dissociation of nucleic acids by ketalized PEI, particle size, ζ potential, morphology, and controlled intracellular delivery of siRNA and plasmid DNA were then evaluated in comparison with unketalized PEI. Results proved that ketalized PEI enhanced both transfection and RNA interference with remarkably reduced cytotoxicity. Surprisingly, intracellular fates of plasmid DNA and siRNA were determined by the molecular weights of ketalized PEI.

Materials

Branched polyethylenimine (HMW PEI, 25 kDa; LMW PEI, 0.8 kDa), 3-(4,5-dimethyl-2-thiazolyl)-2,5-diphenyltetrazolium bromide (MTT), and sodium dodecyl sulfate (SDS) were purchased from Aldrich (Milwaukee, Wis.). N,N-Dimethyl-4-aminopyridine, p-nitrophenyl chloroformate, 2-aminoethanol, pyridinium p-toluenesulfonate, ethyl trifluoroacetate, 2-methoxypropene, molecular sieves, and 1,3-diaminopropane were supplied from Acros (Morris Plains, N.J.). Ethidium bromide was purchased from Fisher Scientific (Pittsburgh, Pa.). Enhanced green fluorescent protein (eGFP)-encoding plasmid DNA was a generous gift from Dr. Pamela Davis (Department of Physiology and Biophysics, Case Western Reserve University). Endotoxin-free plasmid Maxiprep kit was obtained from Qiagen (Valencia, Calif.). Silencer GFP siRNA was purchased from Ambion (Austin, Tex.). NIH 3T3 cells (ATCC, Rockville, Md.) were cultured in Dulbecco's Modified Eagle's medium (DMEM) (MediaTech, Hemdon, Va.) with 10% fetal bovine serum (FBS) (Hyclone, Logan, Utah), unless otherwise specified.

Polymer Characterization

Varian 600 MHz NMR spectrometer (Varian, Palo Alto, Calif.) was used to obtain 1H-NMR spectrum of ketalized and p-nitrophenyl carbamate-activated PEI and 13C-NMR spectrum of p-nitrophenyl carbamate-activated PEI. The molecular weights and molecular weight distributions of p-nitrophenyl carbamate activated PEI and ketalized PEI were determined by a gel permeation chromatography (GPC) system (Waters, Milford, Mass.) equipped with Waters 510 pump, Waters 2414 differential refractive index detector, and Waters 996 photodiode array detector. Two styragel columns (HR 4E, HR 5E; 7.8 mm×300 mm, Waters) preheated to 35° C. in a column heater were used, and N,N-dimethylformamide (DMF) with 10 mM LiBr was used as eluent. Polymer samples were prepared in DMF (0.5 w/v %) and filtered through 0.45 μm PVDF syringe filters before being injected into the GPC system. Samples of 100 μL were run at the eluent flow rate of 1 mL/min. The calibration curves were obtained using polystyrene standards (Polymer Standards Services-USA Inc., Silver Spring, Md.). The molecular weights of ketalized PEI were calculated using the Millennium software program by comparing with elution times of monodispersed polystyrene standards.

Synthesis of Ketalized HMW PEI and LMW PEI (Scheme 2)

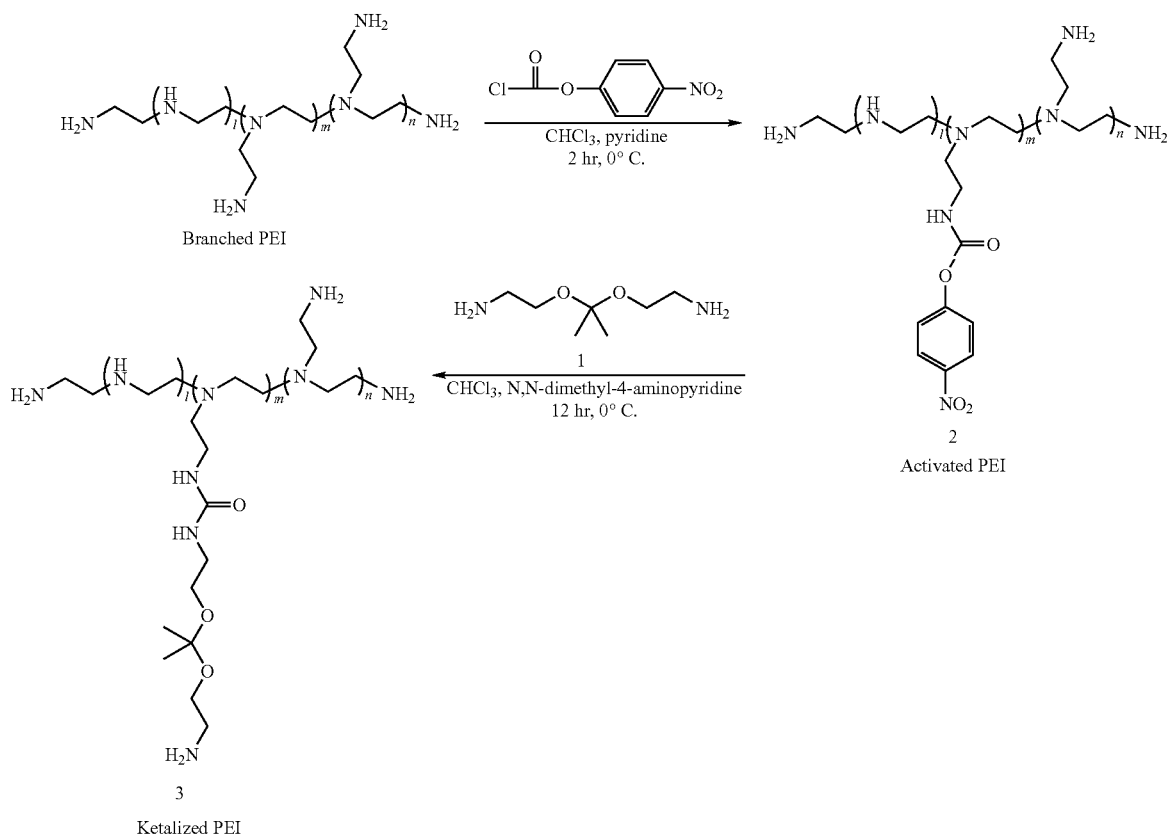

2,2,2-Trifluoro-N-(2-hydroxyethyl)acetamide (Compound 1)

2-Aminoethanol (4 g, 65.48 mmol, 1 equiv) was dissolved in 200 mL of methanol, and triethylamine (9.94 g, 98.23 mmol, 1.5 equiv) was added, followed by adding ethyl trifluoroacetate (11.16 g, 78.59 mmol, 1.2 equiv). After the reaction mixture was stirred overnight at room temperature, the solvent was evaporated, and the residue was dissolved in DI water and extracted with ethyl acetate. The crude product was purified by silica gel column chromatography using ethyl acetate as eluent. The obtained product was a white solid (9.8 g, 62.42 mmol, 95% yield). 1H-NMR (600 MHz, CDCl3): δ

2.07 (s, 1H, CF3CONHCH2CH2OH); δ 3.5 (t, 2H, CF3CONHCH2CH20H); δ 3.8 (t, 2H, CF3CONHCH2CH2OH); δ 6.9 (s, 1H, CF3CONHCH2CH2OH).

N,N'-(2,2'-(Propane-2,2-diylbis(oxy))bis(ethane-2,1-diyl))bis(2,2,2-trifluoroacetamide) (Compound 2)

Compound 1, (9.50 g, 60.51 mmol, 2.5 equiv) was dissolved in 200 mL of tetrahydrofuran (THF), and pyridinium p-toluenesulfonate (PPTS) (0.61 g, 2.42 mmol, 0.1 equiv) was added. After 10 min of stirring, 200 g of molecular sieves (5 Å) was added, and the mixture was stirred for an additional 10 min. 2-Methoxypropene (1.75 g, 24.20 mmol, 1 equiv) was added, and the mixture was stirred for 24 h at room temperature. The molecular sieves were removed by filtration, the solvent was evaporated, and the product was purified using silica gel chromatography. A gradient from 8:1 hexane:ethyl acetate to 2:1 hexane:ethyl acetate, containing 1% (v/v) triethylamine, was used to elute the product that was a white solid after evaporating the solvent overnight (4.12 g, 11.64 mmol, 48% yield). 1H-NMR (600 MHz, CDCl3): δ1.37 (s, 6H,CF3CONHCH2CH2OC(CH3)2 OCH2CH2NHCOCF3); δ 3.5 (s, 8H, CF3CONHCH2CH2OC(CH3)2OCH2CH2NHCOCF3); δ6.8 (s, 2HCF3CONHCH2CH2OC(CH3)2OCH2CH2-NH-COCF3).

1,1'-(2,2'-(Propane-2,2-diylbis(oxy))bis(ethane-2,1-diyl))diurea] (Compound 3)

Compound 2, (4.12 g, 11.64 mmol) was dissolved in 30 mL of 6 M NaOH in water and stirred for 4 h. After being extracted with 5×100 mL of CH2Cl2 from water, the organic layers were evaporated, resulting in amber-colored oil (0.98 g, 6.05 mmol, 52% yield). 1HNMR (600 MHz, CDCl3): δ 1.38 (s, 6H, NH2CH2CH2OC(CH3)2 OCH2CH2NH2); δ 1.49 (s, 4H, NH2CH2CH2OC(CH3)2OCH2CH2NH2); δ 2.85 (t, 4H, NH2CH2CH2OC(CH3)2OCH2CH2NH2); δ 3.46 (t, 4H, NH2CH2CH2OC(CH3)2OCH2CH2NH2).

Para-Nitrophenyl Carbamate-ActiVated PEI (Compound 4)

The ratios of primary, secondary, and tertiary amines of PEI were determined to be 44%, 35%, and 21% for 800 Da PEI, and 35%, 39%, and 26% for 25 kDa PEI using 13C NMR as shown previously. 26 LMW and HMW PEI (0.5 and 0.62 g, 5 mmol of primary amine groups, 1 equiv) was dissolved in 20 mL of freshly distilled CHCl3 and CH2Cl2, respectively. After dry pyridine (1.38 g, 17.5 mmol, 3.5 equiv.) was mixed with the resulting solution, p-nitrophenyl chloroformate (0.61 g, 3.0 mmol, 0.6 equiv) in 40 mL of distilled CHCl3 was added dropwise to the mixture on ice. The reaction mixture was stirred for 2 h on ice. Longer reaction time and higher temperature possibly result in the formation of some amide cross-links because of the reaction of unreacted primary amines or secondary amines with carbamate-activated side chains. This side reaction was minimized by controlling the reaction with slow rate of reactant addition, relatively low concentrations of the reactants, short reaction time, and low reaction temperature. Finally, the pyridinium hydrochloride salt and cross-linked polymer were filtered off under vacuum, and the resulting solution was precipitated in cold diethyl ether with THF. The product obtained was a yellow powder after being dried under vacuum (0.15 g, 0.4 mmol of p-nitrophenyl carbamate groups). Para-nitrophenyl carbamate activation of available primary amines was determined by an integral ratio of the peak at 7.3 ppm to the broad peak at 2.4-2.7 ppm. The yield of the activated LMW PEI was 20% based on the molecular weight determined by MALDITOF analysis (Mp of LMW PEI) 577, mp of p-nitrophenyl carbamateactivated PEI) 872). 1H-NMR (600 MHz, CDCl3): δ 2.4-2.7 (br, —CH2-CH2-NH(H)— and —CH2-CH2-NH-COOArNO2); δ 3.3 (br, —CH2-CH2-NHCOOArNO2); δ 7.3 (br, ArNO2); δ 8.2 (br, ArNO2).

Preparation of Ketalized PEI (Compound 5)

Desired amounts of p-nitrophenyl carbamate-activated LMW and HMW PEI (0.26 mmol of p-nitrophenyl carbamate groups, 1 equiv) were dissolved in 20 mL of freshly distilled $CHCl_3$ and $CH_2Cl_2$, respectively, and N,N-dimethyl-4-aminopyridine (DMAP) (0.19 g, 1.56 mmol, 6 equiv) was added to the solution. The resulting mixture was added dropwise to 20 mL of distilled $CHCl_3$ containing 10-fold molar excess of compound 3 (0.42 g, 2.60 mmol, 10 equiv). The mixture was further stirred for 12 h on ice. The product was then precipitated into cold diethyl ether with THF and dried under vacuum, resulting in a white powder with a hint of yellow color (0.06 g, 53% yield). Ketalization efficiency of primary amines of LMW and HMW PEI was determined as 33% and 35%, respectively, using $^1$H-NMR. $^1$H-NMR (600 MHz, $D_2O$): δ 1.20 (s, —NCH$_2$CH$_2$NHCONHCH$_2$CH$_2$OC(CH$_3$)$_2$ OCH$_2$CH$_2$NH$_2$); δ 2.4-2.6 (m, —CH$_2$—CH$_2$—NH(H)-and-NCH$_2$CH$_2$NHCONHCH$_2$CH$_2$OC(CH$_3$)$_2$ OCH$_2$CH$_2$NH$_2$); δ 2.65 (br, —NCH$_2$CH$_2$NHCONHCH$_2$CH$_2$OC(CH$_3$)$_2$ OCH$_2$CH$_2$NH$_2$); 3.14 (br, —NCH$_2$CH$_2$NHCONHCH$_2$CH$_2$OC(CH$_3$)$_2$ OCH$_2$CH$_2$NH$_2$); δ3.27-3.49 (m, —NCH$_2$CH$_2$NHCONHCH$_2$CH$_2$OC(CH$_3$)$_2$ OCH$_2$CH$_2$NH$_2$, —NCH$_2$CH$_2$NHCONHCH$_2$CH$_2$OC(CH$_3$)$_2$OCH$_2$CH$_2$—NH$_2$, and —NCH$_2$CH$_2$NHCONHCH$_2$CH$_2$OC(CH$_3$)$_2$ OCH$_2$CH$_2$NH$_2$).

Hydrolysis Kinetics of Ketalized PEI

Ketalized PEI (10 mg) was dissolved in 0.6 mL of acetate (pH 5.0 and pH 6.0) and Tris-HCl (pH 7.4) buffer in $D_2O$, respectively, and incubated at 37° C. for various periods of time. The indicators of hydrolysis, disappearance of the ketal linkage peak (1.2 ppm) and appearance of the acetone peak (2.0 ppm), were quantified by comparing with the buffer salt peak using $^1$H-NMR spectroscopy. Half-lives of the various PEI at different pHs were calculated using the Arrhenius equation.

Agarose Gel Electrophoresis Assay

Dissociation of nucleic acids from polyplexes upon hydrolysis was evaluated by a gel retardation assay. Different amounts of unketalized and ketalized PEI predissolved in phosphate buffered saline (PBS) were mixed with 1 μg of DNA in DI water (50 μL in total) to obtain various N/P ratios. The siRNA/polymer polyplexes were formed by the same procedure with 660 ng of siRNA. The resulting polyplexes were then mixed with 5 μL of 10 mM sodium dodecyl sulfate (SDS) solution and incubated for 30 min at room temperature. A 30 μL aliquot of the samples was loaded on a 1.2% agarose gel containing 1 μg/mL ethidium bromide. To evaluate the dissociation of the nucleic acids from the polymers upon hydrolysis, 30 μL of the polyplexes were further incubated for 3 h in the pH 5.0 acetate buffer. Electrophoresis of the DNA/polymer polyplex was run in Tris-borate-EDTA (TBE) buffer at 110 V for 60 min, while electrophoresis of siRNA/polymer polyplex was run in Tris-acetate-EDTA (TAE) buffer at 60 V for 15 min. DNA and siRNA bands were visualized by using a UV transilluminator.

Dynamic Light Scattering Analysis and Transmission Electron Microscopy

Sizes of nucleic acids/ketalized PEI polyplexes were measured by dynamic light scattering (DLS) particle analyzer equipped with a goniometer (BI-240) and BI-9000 digital correlator (Brookhaven Instruments, Holtsville, N.Y.). Measurements were conducted at 25° C., and data were collected at 90° scattering angle. The effective hydrodynamic diameters were analyzed using the CONTIN mode. The sizes and the structures of various polyplexes were analyzed by transmission electron microscopy (TEM). Polyplex solution (2 µL) was dropped on a carbon-coated copper TEM grid (Electron Microscopy Sciences, Hatfield, Pa.) and air-dried for 10 min at 30° C. To obtain hydrolyzed particles, 40 µL of nucleic acids/ketalized PEI polyplex solution was further incubated at 37° C. after being mixed with 40 µL of pH 5.0 acetate buffer. It was confirmed that pH remained at 5.0 after the mixing. After 2 h, 4 µL of the polyplex aliquot was taken for analysis. Electron micrographs were obtained using Philips CM20 transmission electron microscope (Philips Electronic Instruments, Mahwah, N.J.).

Ethidium Bromide Exclusion Assay

The ability of ketalized PEI to condense nucleic acids was confirmed by ethidium bromide exclusion assay. Ethidium bromide (1 µg) was mixed with 1 µg of plasmid DNA or 0.66 µg of siRNA in 40 µL of DI water. After 10 min of incubation at room temperature, various amounts of unketalized and ketalized PEI prepared in 60 µL of DI water were added to the nucleic acid/ethidium bromide mixtures to obtain various N/P ratios. After 30 min of incubation, fluorescence intensity was measured using a fluorescence microplate reader (Molecular Devices, Sunnyvale, Calif.) with an excitation wavelength ($\lambda_{ex}$) of 320 nm and an emission wavelength ($\lambda_{em}$) of 600 nm. Condensation efficiency was inversely quantified by relative fluorescence of the polyplexes, compared with the fluorescence of nucleic acid/ethidium bromide solution without polymer.

Cell Transfection

NIH 3T3 cells were inoculated at a density of $1\times10^5$ cells/well in a 12-well plate, 24 h prior to transfection. DNA/polymer polyplexes were prepared as described above to a final volume of 100 µL and incubated for 30 min at room temperature before being added to a well with an additional 500 µL of DMEM without FBS. The final concentration of DNA in polyplexes was calculated to be 1.66 µg/mL. After 4 h of incubation, the polyplex-containing medium was replaced with 1 mL of fresh DMEM containing 10% FBS, and the cells were further incubated for 24 h at 37° C. The cells were harvested by trysinization, fixed with 2% p-formaldehyde solution for 30 min at 4° C., and then washed with PBS. The relative expression of eGFP fluorescence was analyzed using a Beckman EPICS XL-MCL flow cytometer (Beckman Coulter, Fullerton, Calif.). Transfection efficiency can be quantified by two indicators: transfection rate and gene expression level. In this study, gene activity (i.e., GFP expression) was quantified by comparing average fluorescence intensity of 10000 cells. Therapeutic effects are closely related to how many gene products are produced rather than how many cells are transfected. This is the same principle of the commonly reported luciferase assay, which measures transfection efficiency by protein activity of cells rather than counting transfected cells.

Confocal Microscopy of Intracellular Distribution of Polyplexes

Confocal laser scanning microscopy was used to visualize the intracellular localization of DNA/ketalized PEI polyplexes. NIH 3T3 cells were inoculated at a density of $1.5\times10^4$ cells/well in a 8-well chambered slide (Lab-Tek II, Nalge Nunc, Rochester, N.Y.) 15 h prior to transfection. Ketalized LMW PEI (K-LMW PEI) and ketalized HMW PEI (K-HMW PEI) predissolved in DI water were mixed with 5 µg of DNA in DI water (200 µL total) to achieve the N/P ratio of 40. Each polyplex was incubated for 30 min at room temperature and conjugated with Alexa Fluor 488 dye (Molecular Probes, Inc., Eugene, Oreg.) according to the manufacturer's protocol. Unreacted labeling reagents were removed by using PD-10 size exclusion column (GE Healthcare, Piscataway, N.J.) using DMEM as eluent. 400 µL of polyplex solution containing 0.5 µg of DNA in DMEM was added to each well. After 6 h of incubation, the cells were washed with PBS three times and fixed with 2% p-formaldehyde solution for 30 min at 4° C. Then, the fixed cells were counter-stained with a blue nuclear dye DRAQ5 (BioStatus, Leicestershire, UK) for 20 min and washed with PBS four times. All confocal images were acquired using a Zeiss LSM 510 inverted laser-scanning confocal microscope. A 63× numerical aperture of 1.4 oil immersion planapochromat objective was used for all experiments. Images were collected using a 488 nm excitation light from an argon laser, a 488 nm dichroic mirror, and 500-550 nm band pass barrier filter. All DRAQ5 stained nuclear images were collected using a 633 nm excitation light from a He/Ne2 laser, a 633 nm dichroic mirror, and 650 nm long pass filter.

RNA Interference

NIH 3T3 cells expressing eGFP were prepared by retroviral transduction followed by G418 selection for 10 days.[27] A day prior to siRNA treatment, the cells were seeded at a density of $5\times10^4$ cells/well in a 12-well plate. siRNA/polymer polyplexes were prepared by mixing the solution of eGFP interfering-siRNA as described earlier to a final volume of 100 µL. After being incubated for 30 min at room temperature, the polyplex-containing solutions were added to a cell-containing well with 500 µL of DMEM without FBS. The final concentration of siRNA was adjusted to 1.65 µg/mL. After 4 h of incubation, the polyplex-containing medium was replaced with 1 mL of fresh DMEM containing 10% FBS, and the cells were further cultured for 72 h. Relative eGFP expression was quantified by the same method used for cell transfection.

Cytotoxicity Assay

The cytotoxicity of nucleic acid/polymer polyplexes was evaluated by MTT assay. Briefly, NIH 3T3 cells ($1\times10^4$ and $6\times10^3$ cells/well for DNA transfection and siRNA interference, respectively) were inoculated in 96-well plates. After 24 h, the medium was replaced with mixtures of 50 µL of FBS-free DMEM and 10 µL of the siRNA (7.5 µmol, 99 ng)/polymer solution in DI water, or 50 µL of FBS-free DMEM and 10 µL of the DNA (0.1 µg)/polymer solution in DI water.

The final concentrations of siRNA and DNA in a well were adjusted to 1.65 µg/mL and 1.66 µg/mL, respectively. After 4 h of incubation, the medium was replaced with 100 µL of fresh DMEM containing 10% FBS, and the cells were further incubated for 24 h at 37° C. After removing the medium, 10 µL of 3-(4,5-dimethyl-2-thiazolyl)-2,5-diphenyltetrazolium bromide (MTT) in PBS (10 mg/mL) was added along with 90 µL of medium. The cells were incubated for 3 h at 37° C., then the MTT-containing medium was replaced with 200 µL of DMSO and 20 µL of glycine buffer (0.1 M glycine, 0.1 M NaCl) to dissolve the formazan crystal formed by live cells. The relative viability of the cells in each well was measured by UV absorbance at 561 nm.

Statistics. For statistical analysis, triplicate data were analyzed using Analysis Of Variance (ANOVA) with a Student's t-test on the significance level of $p<0.01$ and presented as mean±standard deviation.

Ketalization of PEI

New PEI-derived biodegradable polymers were designed to provide a number of advantages for intracellular gene delivery processes. First, hydrolysis of ketal branches contributes to endosomal disruption by osmotic pressure due to increased number of small molecules in the endosome and swelling of the polyplexes generated by lessened attractive interactions between nucleic acids and hydrolyzed polymer. This process can help endosomal escape of the polyplexes, independent of the hypothetical proton sponge effect. Second, the hydroxyl arms generated after hydrolysis of the ketalized PEI also greatly diminish attractive interactions with nucleic acid and release it to the cellular targets, followed by enhanced access by cellular machinery for gene expression. Third, the hydrolyzed polymer is also expected to interact with endogenous DNA less attractively, reducing the possibility of generating undesirable side effects such as cytotoxicity.28 Specifically, K-LMW PEI was hypothesized to be able to transfect cells through enhanced endosomal escape and efficient DNA dissociation from the cationic backbone of the polymer after hydrolysis because it was reported that LMW PEI was able to form polyplexes with DNA but could not transfect cells due to its limited buffering capacity.

Figure 2:
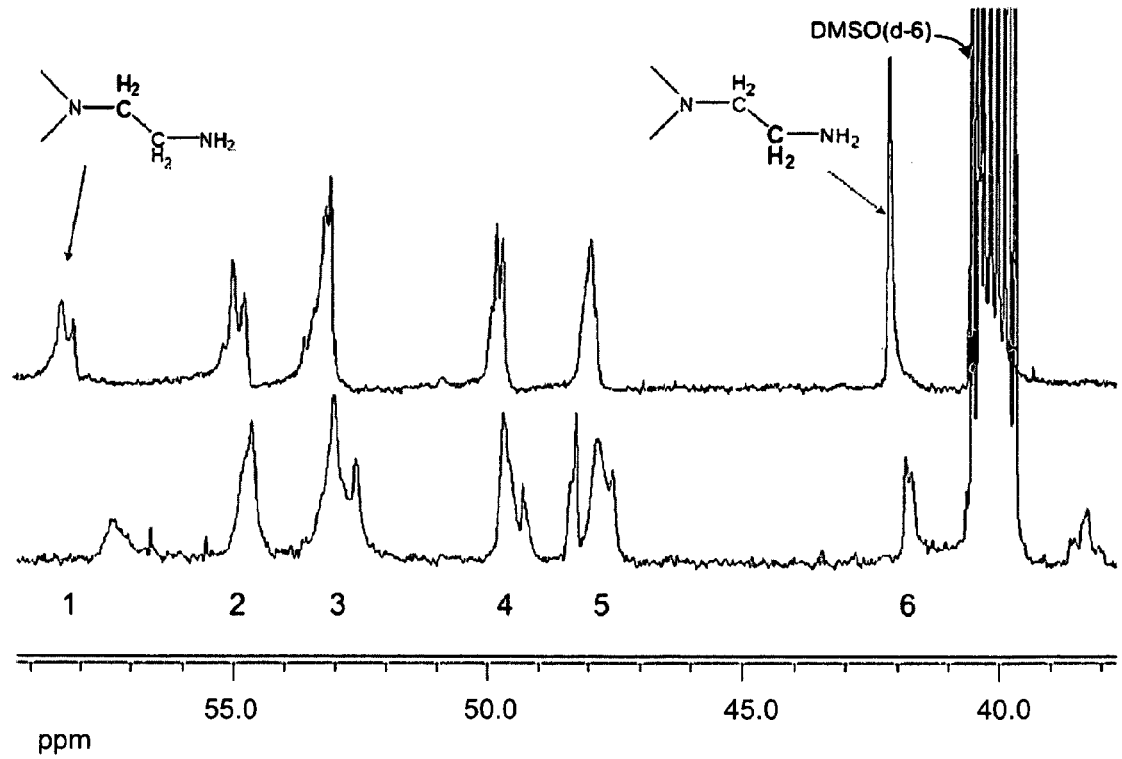
FIG. 2 illustrates 13C-NMR spectrum of LMW PEI (above) and p-nitrophenyl carbamate-activated LMW PEI (below).

Ketalized PEI was prepared by conjugating excess diamine ketal (compound 3) to p-nitrophenyl carbamate-activated PEI (compound 4) (Scheme 2). para-Nitrophenyl carbamateactivated LMW PEI was characterized by $^1$H-NMR and $^{13}$CNMR as shown in FIGS. 1 and 2. The degree of p-nitrophenyl carbamate activation for available primary amines was confirmed by integral ratio of phenyl protons (7.3 and 8.2 ppm) to methylene protons (2.4-2.7 ppm) of PEI. Importantly, selective activation of primary amines by carbamate over secondary amines was confirmed by $^{13}$C-NMR spectrum (FIG. 2). The intensity of no. 1 and no. 6 peaks assigned to methylene groups between primary amines and tertiary amines was significantly reduced, while the other methylene peaks (no. 2, no. 3, no. 4, and no. 5), representing carbons associated with secondary amines and tertiary amines, did not change significantly. Therefore, $^{13}$C-NMR clearly confirmed that primary amines were predominantly activated with carbamate over secondary and tertiary amines.

Figure 3:
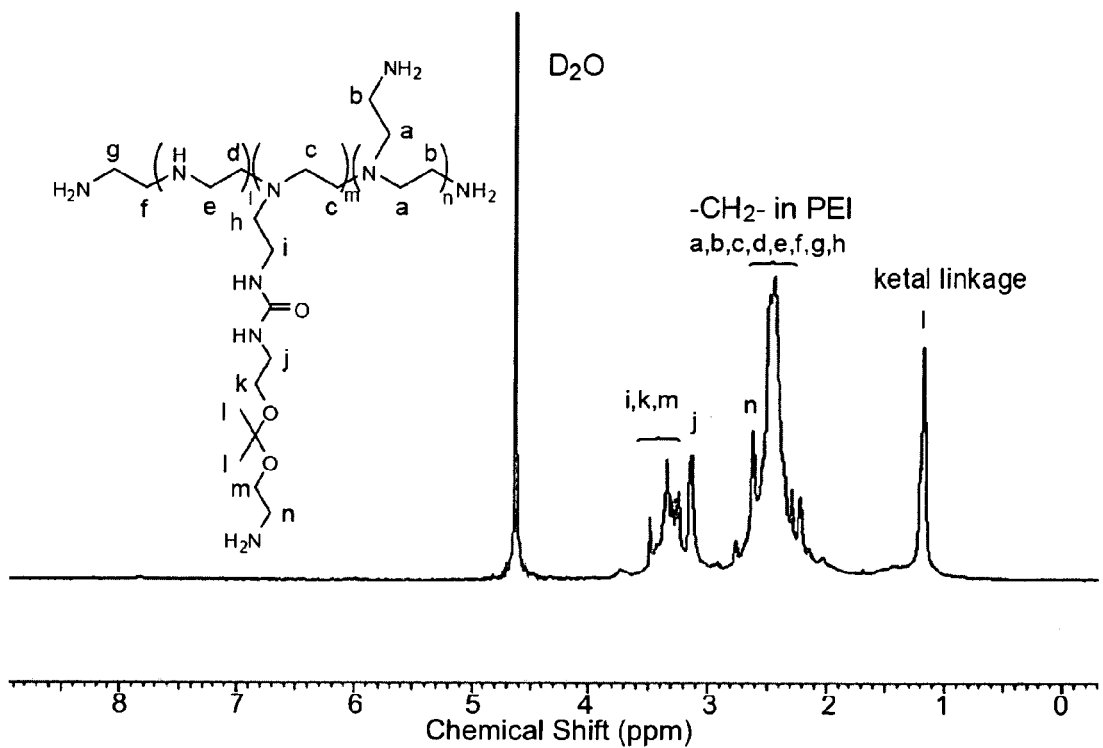
FIG. 3 illustrates 1H-NMR spectrum of ketalized LMW PEI.

The K-LMW PEI was characterized by $^1$H-NMR (FIG. 3). $^1$H-NMR spectrum of ketalized PEI indicated a sharp singlet peak at 1.2 ppm (i.e., methyl protons of ketal linkage). Also, after ketal diamines reacted with the carbamate-activated PEI, p-nitrophenyl proton peaks positioned at 7.3 and 8.2 ppm disappeared completely, indicating that ketal diamines were conjugated to most of carbamate-activated branches. Ketalization efficiency to available primary amines was roughly determined to be approximately 33% for K-LMW PEI and 35% for K-HMW PEI by integral ratios of the peak at 1.2 ppm to the peak at 2.4-2.6 ppm.

Molecular weight distributions of the p-nitrophenyl carbamate-activated and ketalized PEI were determined by GPC analysis and referred to monodispersed polystyrene standards (Table 1). For example, the molecular weights of the p-nitrophenyl carbamate-activated LMW PEI (A-LMW PEI) measured by UV detection at 310 nm were $M_n$) 878 and $M_w$) 1149 with polydispersity index (PDI) of 1.31. It was confirmed that $M_n$ of A-LMW PEI from GPC analysis was consistent with the one based on carbamate-activation efficiency quantified by $^1$H-NMR (FIG. 1).

TABLE 1

GPC analysis of ketalized and p-nitrophenyl carbamate-activated PEI

| Polymer | Elution volume (mL) | $M_n$ | $M_w$ | PDI |
|---|---|---|---|---|
| K-HMW PEI | 18.17 | 17194 | 25964 | 1.51 |
| A-HMW PEI | 17.91 | 20305 | 31672 | 1.56 |
| K-LMW PEI | 21.60 | 1150 | 1472 | 1.28 |
| A-LMW PEI | 21.87 | 878 | 1149 | 1.31 |

Activated PEI with p-nitrophenyl carbamate reacts with amino groups of ketal diamines (compound 3) and free amino groups of the unactivated and activated PEI, generating inter- and intracrosslinked polymers. It was confirmed that inter-crosslinking of activated PEI was minimized (Table 1) or inter-crosslinked polymers were effectively removed by filtration by comparing with the MWs and PDIs of the starting materials (i.e., PDI) 1.33 and 1.41 for LMW and HMW PEI, respectively). It was very difficult to characterize intra-crosslinked polymers because only a part of the primary amine was ketalized and partially intra-crosslinked PEI would not provide distinctive analytical changes. To quantitatively estimate a possibility of intracrosslinking of activated PEI, 1-amino-3,3-diethoxypropane was reacted with p-nitrophenyl carbamate at 0° C. in the presence of pyridine or DMAP. Calculated reaction rate constants showed 5 times slower rate of diamide formation in the presence of pyridine compared with using DMAP. Without pyridine nor DMAP, the reaction was negligibly slow. Therefore, p-nitrophenyl carbamate groups of activated PEI are not expected to efficiently react with free amino groups of other PEI or its own in the presence of pyridine, while p-nitrophenyl carbamate groups mostly reacting with excess ketal diamines are expected to have enormously increased reaction rate when DMAP is used as a catalyst. These significantly different reaction rates and reaction conditions of excess ketal diamines (compound 3) enabled synthesis of ketalized PEI with minimal intra-crosslinking.

Another type of evidence was obtained by quantifying the amount of primary amines of unmodified, activated, and ketalized PEI, respectively. Amine quantification using TNBS assay showed that numbers of amine groups per unmodified and ketalized LMW PEI were consistent. If carbamate-activated PEI had significantly reacted with primary amines of other PEI or its own, residual primary amine concentration after ketalization should have been decreased.

Acid-Sensitivity of Ketalized PEI

Figure 4:
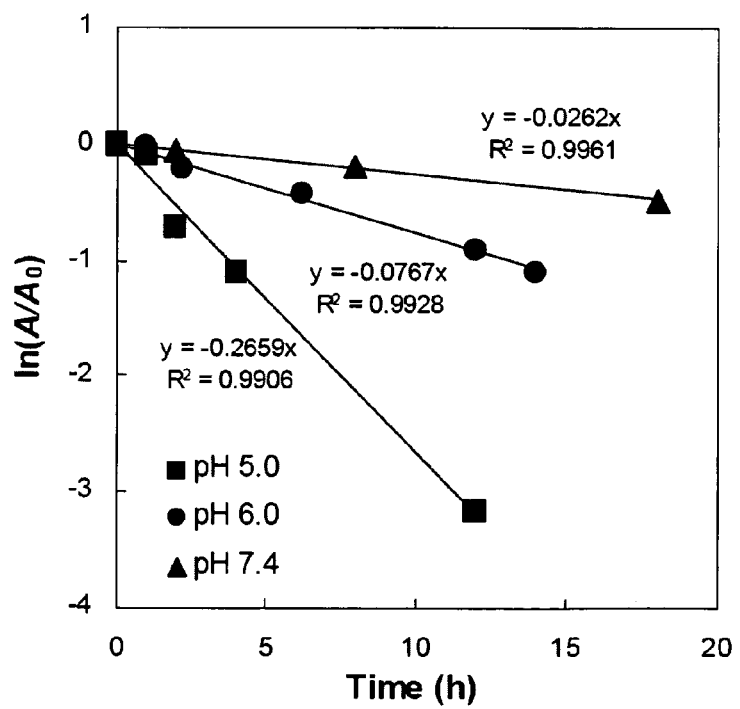
FIG. 4 illustrates a graph showing hydrolysis kinetics of ketalized LMW PEI at pH 5.0, 6.0, and 7.4 (A and A0 represent integrations of ketal linkage peaks after a certain period of incubation time and before hydrolysis, respectively).

Hydrolysis of ketalized PEI at endosomal pH 5.0 and physiological pH 7.4 was investigated by incubating K-LMW PEI in acetate and Tris-HCl buffers in $D_2O$ at 37° C. for various periods of time, and the disappearance of the ketal linkage peak at 1.2 ppm was compared with the constant buffer salt peak. As shown in FIG. 4, the half-lives of ketalized PEI at pH 5.0, 6.0, and 7.4 were calculated to be 2.6, 9.0, and 26.4 h, respectively. The result shows that the hydrolysis rate of the ketalized PEI at endosomal pH of 5.0 is approximately 10 times faster than at physiological pH of 7.4. Compared with a water-insoluble ketalized polymer, which showed 3 times faster hydrolysis at pH 5.0 than at pH 7.4, 25 K-LMW PEI showed 10 times more acid sensitivity to acidic environments. K-HMW PEI also showed a quite similar acid sensitivity to K-LMW PEI with similar solubility in aqueous solutions.

Efficient Condensation of Nucleic Acids at High N/P Ratios by Ketalized PEI

Condensation of nucleic acids to be internalized by cells is an important prerequisite for efficient gene delivery using cationic polymers. The condensation efficiency of various PEI was quantified by size shrinkage of the polyplexes and ethidium bromide exclusion. As shown in FIG. 5A, the size of DNA/HMW PEI polyplexes above the N/P ratio of 5 was around 120 nm and relatively constant at higher N/P ratios. Conversely, the most compact DNA/K-LMW PEI polyplex (about 150 nm) was obtained at the N/P ratio of 40. DNA/K-HMW PEI polyplexes (i.e., about 250 nm) were larger than DNA/K-LMW PEI polyplexes whose size (i.e., about 150 nm) was close to the size of DNA/HMW PEI polyplexes at the N/P ratio of 40 and above (FIG. 5A). The smallest size of DNA/LMW PEI polyplexes was around 500 nm at the N/P ratios of 40 and above, indicating limited condensation of nucleic acids by LMW PEI. Diameters of ketalized PEI polyplex particles decreased exponentially up to the N/P ratio of 40. As previously reported, siRNA/PEI polyplexes were slightly smaller than DNA/PEI polyplexes, regardless of molecular weights, yet siRNA/PEI polyplexes showed a size trend similar to the one of DNA/PEI polyplexes (FIG. 5B). Regardless of molecular weights, ketalized PEI resulted in similar sized polyplexes with siRNA, while larger ketalized PEI resulted in larger polyplexes with plasmid DNA (FIG. 5A).

This finding suggests importance of molecular weight and structure of cationic polymer in nucleic acid condensation as reported previously. HMW PEI can intertwine with both plasmid DNA and siRNA, while LMW PEI cannot efficiently condense but be absorbed on nucleic acids which are significantly larger than LMW PEI. Ketalization seems to play differently on HMW and LMW PEI. Ketalization adds bulky side arms to HMW PEI, which spatially interferes interactions with nucleic acids, especially plasmid DNA (about 5 kbp), which is significantly longer than siRNA (23 bp). On the contrary, K-LMW PEI could efficiently interact with both plasmid DNA and siRNA, and the both particle sizes were similar to each other (FIG. 5A-B). One possible explanation is that amino ketal arms, which might be sufficiently long compared with LMW PEI, provide flexibility for the polymer to interact with nucleic acids attractively. In contrast, the amino ketal arms in HMW PEI are significantly shorter than the polymer and serve as bulky spikes hindering close interaction with nucleic acids. Zeta potential analysis demonstrated that ketalization of HMW PEI decreased the surface charge of the polyplexes, while ketalization of LMW PEI did not significantly affect the surface charge of the polyplexes. Thus, it also implies that ketalization of HMW PEI reduced efficiency of nucleic acid condensation.

The capability of various PEI to condense nucleic acids was also confirmed by measuring the shielded fluorescence of ethidium bromide intercalated with nucleic acids. For both ketalized and unketalized PEI, relative fluorescence of polyplexes dramatically decreased with N/P ratios up to 10, implying shielding of nucleic acids in the polyplexes (FIG. 6). At N/P ratios below 10, HMW PEI showed the best condensation of both plasmid DNA and siRNA, but both K-LMW and K-HMW PEI showed poor condensation efficiency. At high N/P ratios, however, K-LMW PEI showed enhanced nucleic acid condensation efficiency, although complexation of plasmid DNA by LMW PEI was still very poor, even at high N/P ratios (e.g., N/P>40) (FIG. 6A). This indicates that DNA condensation of LMW PEI was enhanced by the ketalization. FIG. 6B shows siRNA condensation efficiency by various PEI. Interestingly, more efficient fluorescence quenching was observed with siRNA-containing polyplexes except those made of HMW PEI, which efficiently compacted both plasmid DNA and siRNA (FIGS. 5 and 6). Nucleic acids/K-HMW PEI exhibited relatively low condensation efficiency, even at high N/P ratios (FIGS. 5 and 6). This result is implicit evidence that amino ketal branches play a different role in HMW and LMW PEI. As previously discussed for FIG. 5, long and bulky ketal branches in HMW PEI could impair the structural flexibility of PEI, preventing efficient nucleic acids condensation. In contrast, K-LMW PEI might be able to efficiently interact with nucleic acids due to enhanced flexibility provided by long ketal branches. Because amine modification with nondegradable branches showed no significant changes in DNA condensation efficiency compared with K-LMW PEI, ketalization may be the major cause of changes in DNA condensation.

Efficient Dissociation of Nucleic Acids from Polyplexes of Ketalized PEI upon Hydrolysis Formation of nucleic acids/ketalized PEI polyplexes at the various N/P ratios and the dissociation of nucleic acids from the polyplexes upon hydrolysis were demonstrated by agarose gel electrophoresis. For polyplexes made of unketalized PEI, migration of nucleic acids was completely impeded when the N/P ratio was 5 or higher, proving that both LMW and HMW PEI efficiently compensated the negative charges of nucleic acids even though LMW PEI has inefficient gene transfection activity. The migration of nucleic acids was completely impeded at the N/P ratio of 20 or higher for nucleic acids/ketalized PEI polyplexes, indicating that ketalized PEI could efficiently compensate the negative charges of nucleic acids at relatively higher N/P ratios than unketalized PEI. However, it was clearly demonstrated that the hydrolysis of ketal linkages at mild acidic pH 5.0 freed nucleic acids from the polyplexes even at the N/P ratio of 80. These results clearly suggest efficient release of nucleic acids from the polyplexes made of ketalized PEI upon hydrolysis in the acidic endosome.

Morphological Changes of Polyplexes upon Hydrolysis

Transmission electron micrographs presenting the sizes and the morphologies of various nucleic acid/polymer polyplexes before and after hydrolysis were performed. The formation of relatively spherical and compact DNA/HMW PEI and siRNA/HMW PEI polyplexes with a diameter of 50-90 nm was shown. Likewise, DNA/K-LMW PEI polyplexes (diameter of 100-120 nm) and siRNA/K-LMW PEI polyplexes (diameter of 80-90 nm) were also spherical and compact, indicating that nucleic acids/K-LMW PEI polyplexes are able to considerably protect their cargos against nuclease degradation. However, DNA/K-HMW PEI polyplexes were somewhat larger in size compared to DNA/HMW PEI polyplexes, implying that complexation efficiency of K-HMW PEI was less efficient than HMW PEI and K-LMW PEI, possibly as a result of steric hindrance from ketalized branches. Very few DNA/LMW PEI and siRNA/LMW PEI polyplexes were observed under TEM due to inefficient complexation of DNA and siRNA by LMW PEI, although ethidium bromide had very limited accessibility to the polyplexes. This suggests that LMW PEI interacts with nucleic acids by electrostatic attractions but cannot condense them as a form of nanoparticles (FIG. 6). From TEM images of DNA polyplexes and siRNA polyplexes, it was observed that DNAFigure containing polyplexes were larger than siRNA-containing polyplexes because of the different sizes of nucleic acids (5 kbp plasmid DNA and 22 bp siRNA), as reported previously. TEM images showed swollen and/or destructed structures of nucleic acids/ketalized PEI polyplexes upon hydrolysis. The destructed structure of polyplexes made of ketalized PEI was particularly well observed with DNA/K-LMW PEI and DNA/K-HMW PEI polyplexes. Evaporation of hydrolysis products (i.e., acetone and ethanolamine) from the ketalized PEI during preparation of the microscopy study left holes, destabilizing the structure of the hydrolyzed polyplexes. These destructed structures of polyplexes demonstrated that branches of ketalized PEI were hydrolyzed effectively at mild acidic environments followed by releasing nucleic acids from cationic polymer backbone.

Enhanced Transfection by Ketalized LMW PEI

Murine fibroblast NIH 3T3 cells were incubated with polyplexes containing enhanced green fluorescent protein (eGFP)-encoding plasmid DNA with either unketalized or ketalized PEI. Transfection efficiency was quantified by relative fluorescence of the cells by flow cytometry. K-LMW PEI remarkably enhanced transfection efficiency at high N/P ratios compared with LMW PEI, which showed no measurable gene expression over the full range of N/P ratios (FIG. 7A). The transfection efficiency of K-LMW PEI at N/P ratios of 40-80 was even significantly higher than that of HMW PEI, which has been known to be the most potent PEI. Unexpectedly, however, completely diminished transfection was observed with DNA/K-HMW PEI polyplexes. Regardless of N/P ratios and molecular weights, no noticeable cytotoxicity was observed for all ketalized PEI (FIG. 7B). On the contrary, HMW PEI showed significant cytotoxicity at high N/P ratios (i.e., N/P ratio of 10 and above) (FIG. 7B), and it should be noted that an insufficient number of cells were collected for transfection analysis after being incubated with HMW PEI at N/P ratio of 40 and above (FIG. 7A). Ketalized 10 kDa PEI, middle molecular weight (MMW) PEI, showed intermediate transfection efficiency between K-LMW and K-HMW PEI, indicating that transfection efficiency by ketalized PEI was inversely proportional to molecular weights.

In this study, it was shown that K-LMW PEI, which is small enough to be excreted from the body, could transfect cells even more efficiently than HMW PEI with reduced cytotoxicity at high N/P ratios, suggesting a possibility of utilizing K-LMW PEI for clinical gene therapy. Using human cervical cancer HeLa cells, unketalized HMW PEI showed higher transfection efficiency than K-LMW PEI, although ketalization still significantly enhanced transfection efficiency of LMW PEI. This is probably because epithelial cells (e.g., HeLa) have different internalization and intracellular processes from fibroblasts (e.g., NIH 3T3). According to internalization inhibition experiment, the polyplexes synthesized using ketalized PEI were internalized differently from unketalized PEI polyplexes. Internalization of DNA/unketalized PEI polyplexes was inhibited exclusively by endocytosis inhibitors, while internalization of DNA/ketalized PEI polyplexes was inhibited by both endocytosis and macropinocytosis inhibitors. This is probably due to larger size of DNA/ketalized PEI polyplexes than DNA/unketalized PEI polyplexes (FIG. 5).

It is very well known that cationic particles aggregate significantly in the presence of serum protein. Transfection efficiency of K-LMW PEI polyplexes was not significantly affected by the presence of 10% serum at low N/P ratios, indicating that K-LMW PEI polyplexes were found less aggregating in 10% serum than HMW PEI polyplexes at low N/P ratios. At high N/P ratios, however, transfection efficiency of K-LMW PEI polyplexes dropped significantly while HMW PEI polyplexes showed slightly decreased transfection efficiency. This implies that K-LMW PEI polyplexes need to be PEGylated to reduce aggregation for in vivo gene delivery. However, it should be noted that HMW PEI polyplexes are significantly more toxic than K-LMW PEI polyplexes at high N/P ratios.

Because dissociation of nucleic acids from K-HMW PEI after hydrolysis was as efficient as from K-LMW PEI, one reason for low transfection efficiency of DNA/K-HMW PEI polyplexes might be ascribed to long and bulky ketalized branches interfering condensation (FIGS. 5A and 6A), which prevents nuclear localization through nuclear pores. It was previously shown that the compact structure of DNA/PEI polyplexes needs to be maintained until it is transported into the nucleus, as free DNA can diffuse only very slowly in the cytoplasm. To verify the hypothesis, polyplexes synthesized with K-HMW and K-LMW PEI were incubated with cells and their intracellular distributions were examined. It was clear that DNA/K-HMW PEI polyplexes were found only in the cytoplasm, while some of the DNA/K-LMW PEI polyplexes were found in the nucleus. Therefore, it was proved that molecular weights of ketalized PEI determine the intracellular fate of the polyplexes. Quantitative effect of ketalization ratio on intracellular localization is currently under investigation.

Because acetylated PEI and cross-linked LMW PEI showed enhanced transfection, contribution of acid-degradability of ketalized PEI to the enhanced transfection was investigated by comparing with transfection using nondegradable diamineconjugated LMW PEI. This nondegradable LMW PEI was synthesized by conjugating p-nitrophenyl carbamate-activated PEI with excess 1,3-diaminopropane instead of acid-degradable amine-bearing ketals. As shown in FIG. 8A, transfection efficiency of the acid-degradable K-LMW PEI was much higher than that of LMW PEI conjugated with nondegradable branches even though nondegradable modified LMW PEI showed better GFP expression compared to unmodified LMW PEI. This result confirmed that enhanced transfection efficiency of the K-LMW PEI can be attributed to acid degradability of the polyplexes. As shown in FIG. 8B, addition of branches reduces cytotoxicity regardless of their degradability, although a little lower cytotoxicity was observed with DNA/K-LMW PEI polyplexes than with DNA/nondegradable LMW PEI polyplexes. This result implies that hydroxyl-bearing branches of hydrolyzed PEI generate lowered cytotoxicity to a certain extent, possibly due to less attractive interactions with chromosomal nucleic acids.

Efficient RNA Interference by K-HMW PEI. From DNA transfection results, ketalization of HMW-PEI reduced transfection efficiency of the polymer, although plasmid DNA was efficiently released from K-HMW PEI polyplexes upon hydrolysis (FIG. 7A). The lowered transfection efficiency by DNA/K-HMW PEI polyplexes seemed to be resulted from weakened DNA condensation, which resulted in poor nuclear delivery but was possibly enough for cytosolic release of their cargos. In other words, K-HMW PEI may be a more efficient carrier for siRNA interfering mRNA in the cytoplasm than for delivery of plasmid DNA to the nucleus due to inefficient condensation by long and bulky ketalized branches. This hypothesis was supported by the result that K-HMW PEI delivered anti-eGFP siRNA to eGFP expressing NIH 3T3 cells more efficiently than K-LMW PEI, as shown in FIG. 9A. While unketalized HMW PEI showed a significant inhibition of GFP expression (inhibition degree: 65.9 (1.8%) at the N/P ratio of 20 mainly due to high cytotoxicity decreasing normal gene expression (FIG. 9B), K-HMW PEI exhibited comparable GFP suppression efficiency (inhibition degree: 65.7 (1.0%) as HMW PEI at the N/P ratio of 80 with remarkably reduced cytotoxicity (FIG. 9B). Again, an insufficient number of cells were collected for analysis after being incubated with siRNA/HMW PEI polyplexes at high N/P ratios due to intolerable cytotoxicity (FIG. 9A). siRNA/KLMW PEI polyplexes showed a slight GFP inhibition (ca. 20%) at the high N/P ratio of 100, where they showed a superior DNA transfection efficiency. Unketalized LMW PEI showed consistently slight interferences for all ranges of the N/P ratios without any cytotoxicity. Negligible cytotoxicity was observed with all ketalized PEI regardless of N/P ratios, types of nucleic acids, and molecular weights (FIGS. 7 and 9). From transfection and RNA interference by unketalized and ketalized PEI, therefore, it can be concluded that ketalization reduces cytotoxicity of PEI and molecular weights of ketalized PEI determine intracellular fates of polyplexes.

EXAMPLE 2

Example 1 demonstrated that PEI partially conjugated with acid labile ketal linkages to primary amines of branched PEI enhanced transfection and RNA interference efficiencies with almost completely diminished cytotoxicity. In this example, we further show the ability to precisely control intracellular fates of nucleic acids/ketalized PEI polyplexes by differentially modulating ketalization ratios of PEI in the range of about 17% to about 96%. Results demonstrated that nucleic acid condensation efficiency, transfection activity, and RNA interference of ketalized PEI were consequently associated with intracellular localizations that were explicitly dependent on ketalization ratios and molecular weights of the polymer as well as types of gene cargos. This study implies that differentially selective delivery of nucleic acids to appropriate intracellular targets can be accomplished by tailoring the structure of polymeric gene carriers.

Materials

Branched polyethylenimine (high molecular weight, 25 kDa; low molecular weight, 0.8 kDa) and 3-(4,5-dimethyl-2-thiazolyl)-2,5-diphenyltetrazolium bromide (MTT) were purchased from Aldrich (Milwaukee, Wis., USA). N,N-dimethyl-4-aminopyridine, p-nitrophenyl chloroformate, 2-aminoethanol, pyridinium p-toluenesulfonate, ethyl trifluoroacetate, 2-methoxypropene, and molecular sieves were supplied from Acros (Morris Plains, N.J., USA). Ethidium bromide was purchased from Fisher Scientific (Pittsburgh, Pa., USA). Enhanced green fluorescent protein (eGFP)-encoding plasmid DNA (pDNA, 5.0 kbp) was a generous gift from Dr. Pamela Davis (Department of Biophysics, Case Western Reserve University, Cleveland, Ohio, USA). Alexa Fluor 488 dye was purchased from Molecular Probes (Eugene, Oreg., USA), and DRAQ5 nuclear dye was purchased from BioStatus (Leicestershire, UK). Silencer® GFP siRNA was purchased from Ambion (Austin, Tex., USA). NIH 3T3 cells purchased from ATCC (Rockville, Md., USA) were cultured in Dulbecco's Modified Eagle's medium (DMEM) (MediaTech, Herndon, Va., USA) with 10% fetal bovine serum (FBS) (Hyclone, Logan, Utah, USA), unless otherwise specified.

Characterization of ketalized PEI by GPC

Ketalized PEI was prepared as shown Example 1 with moderate modifications to control ketalization ratios (More detailed synthesis procedures and confirmation in Supplementary information). The yields of the final products were calculated using the molecular weights of each ketalized and starting material PEI by gel permeation chromatography (GPC) analysis. Ketalization ratios of ketalized PEI was quantified by using $^1$H-NMR spectra obtained using a Varian 600 MHz NMR spectrometer (Varian, Palo Alto, Calif., USA) (Details in mentary information). The molecular weights and molecular weight distributions of the intermediate p-nitrophenyl carbamate-activated PEI and ketalized PEI were measured by using a GPC system (Waters, Milford, Mass., USA) equipped with Waters 510 pump, Waters 2414 Differential Refractive Index Detector, and Waters 996 Photodiode Array Detector. Two styragel columns (HR 4E, HR 5E; 7.8 mm×300 mm, Waters) pre-heated to 35° C. in a column heater were used, using N,N-dimethylformamide (DMF) with 10 mM LiBr as the eluent. Polymer samples dissolved in 0.5% (w/v) DMF were filtered through 0.45 µm PVDF syringe filters, and 100 µL of polymer solution was injected into the GPC system. The flow rate of the eluent was set to 1 mL/min. The molecular weights of ketalized PEI were calculated using the Millennium software program by comparing with elution times of monodispersed polystyrene standards (Polymer Standards Services-USA Inc., Silver Spring, Md., USA).

Determination of Hydrolysis Kinetics of Ketalized PEI

To evaluate the kinetics of hydrolysis of ketalized PEI with different ketalization ratios at pH 5.0 and pH 7.4, ketalized low molecular weight PEI (K-LMW PEI) was dissolved in pH 5.0 acetate and pH 7.4 Tris-HCl buffers in $D_2O$, respectively, and incubated at 37° C. for various periods of time. Disappearance of the ketal linkage peak (1.2 ppm) was measured by $^1$H-NMR. Hydrolysis kinetics was quantified by comparing the disappearance of the ketal linkage peak with the constant buffer salt peak.

Dynamic Light Scattering (DLS) Analysis

Sizes of nucleic acids/ketalized PEI polyplexes were measured by dynamic light scattering (DLS) particle analyzer equipped with a goniometer (BI-240) and BI-9000 digital correlator (Brookhaven Instruments, Holtsville, N.Y.). Two micrograms nucleic acids (i.e., pDNA and siRNA) with various amounts of ketalized PEI were mixed in 100 µL of deionized (DI) water at various N/P ratios, and the resulting polyplex solution was diluted with additional 800 µL of DI water, followed by its incubation for 30 min at room temperature.

Triplicate measurements for each sample were performed at 25° C., and data were collected at 90° scattering angle. The diameters of particles were analyzed using the CONTIN mode.

Ethidium Bromide Exclusion Assay

Nucleic acid condensation efficiency of ketalized PEI was monitored by a standard ethidium bromide exclusion assay. One microgram of ethidium bromide was mixed with 1 μg of pDNA or 0.66 μg of siRNA in 40 μL of DI water. After 10 min of incubation at room temperature, various amounts of unketalized and ketalized PEI dissolved in 60 μL of DI water were added to the nucleic acids/ethidium bromide mixtures to obtain various N/P ratios. After 30 min of incubation, fluorescence intensity was measured using a fluorescence microplate reader (Molecular Devices, Sunnyvale, Calif., USA) with an excitation wavelength ($\lambda_{ex}$) of 320 nm and an emission wavelength ($\lambda_{em}$) of 600 nm. The fluorescence of pDNA/ethidium bromide solution without polymers was set to 1, while the background fluorescence of ethidium bromide without nucleic acids was set to 0. Reduced fluorescence was used as a quantitative indicator of nucleic acid condensation in polyplexes.

Cell Transfection

NIH 3T3 cells were inoculated at a density of $1\times10^5$ cells/well in a 12-well plate, 24 h prior to transfection. pDNA/polymer polyplexes were prepared by mixing 1 μg of pDNA in 50 μL of DI water with various amounts of unketalized and ketalized PEI stock solutions in PBS, resulting in various N/P ratios in the final volume of 100 μL. Prepared pDNA/polymer polyplexes were incubated for 30 min at room temperature and added to triplicate wells with an additional 500 μL of DMEM. The final concentration of pDNA in polyplexes was calculated to be 1.66 μg/mL. After 4 h of incubation, the medium was replaced with 1 mL of fresh DMEM supplemented with 10% FBS, and the cells were further incubated for 24 h at 37° C. Cells were harvested by trypsinization, fixed with 2% p-formaldehyde solution for 30 min at 4° C., and then washed with PBS. The relative expression of eGFP fluorescence of $1\times10^4$ cells was analyzed using Beckman EPICS XLMCL flow cytometer (Beckman Coulter, Fullerton, Calif., USA), and relative transfection efficiency was quantified by comparing average fluorescence intensities of the cells incubated with various pDNA/PEI polyplexes.

RNA Interference eGFP-expressing NIH 3T3 cells were prepared by retroviral transduction followed by G418 selection for 10 days. A day prior to siRNA treatment, the cells were seeded at a density of $5\times10^4$ cells/well in 12-well plate. siRNA/polymer polyplexes were prepared by mixing the solution of eGFP interfering-siRNA (75 μmol, 990 ng) to a final volume of 100 μL as described earlier in the preparation of DNA-containing polyplexes. Then 100 μL of the resulting polyplex solutions were incubated for 30 min at room temperature and added to cells with 500 μL of DMEM without FBS. The final concentration of siRNA was adjusted to 1.65 μg/mL. After 4 h of incubation, the medium in the 12-well plate was replaced with 1 mL of fresh DMEM supplemented with 10% FBS, and the cells were further cultured for 72 h. The silencing of eGFP gene expression was quantified by average fluorescence intensities of the cells incubated with various siRNA/PEI polyplexes in comparison with the cells incubated without polyplexes.

Confocal Laser Scanning Microscopy

Confocal laser-scanning fluorescent microscopy was performed to visualize the intracellular localizations of various nucleic acid/ketalized PEI polyplexes. NIH 3T3 cells were inoculated at a density of $2.0\times10^4$ cells/well in a Falcon 8-well cultureslide (BD Biosciences, Franklin Lakes, N.J., USA), 15 h prior to the incubation with the polyplexes. Desired amounts of various K-LMW PEI and K-HMW PEI solution in DI water were mixed with 4 μg of luciferase plasmid DNA (5.9 kbp) or siRNA in DI water (400 μL total) to achieve the N/P ratio of 60, respectively. The polyplexes were incubated for 30 min at room temperature and then conjugated with Alexa Fluor 488 succinimidyl ester (Molecular Probes, Inc., Eugene, Oreg., USA) which reacts with primary amines of PEI, by following the manufacturer's protocol. Unreacted labeling reagents were filtered by PD-10 size exclusion column (GE Healthcare, Piscataway, N.J., USA) using DMEM as eluent. 520 μL of polyplex solution containing 0.6 μg of pDNA or siRNA in DMEM was added to each well. After 6 h of incubation, the cells were washed with PBS four times and fixed with 2% p-formaldehyde solution for 30 min at 4° C. Then, the fixed cells were counter-stained using 1 μM nuclear dye DRAQ5 solution (BioStatus, Leicestershire, UK) in PBS for 20 min, followed by being washed with PBS four times. Using an Olympus IX2 inverted microscope coupled with a Fluoview 1000 confocal scanning microscopy setup (FV10-ASW, Olympus America, Inc., Melville, N.Y., USA), cellular images were viewed with a 40×/1.3 NA oil immersion planapochromat objective. Images of Alexa Fluor 488 were collected using a 488 nm excitation light from a multiple argon laser, a 488 nm dichroic mirror, and a 505-605 nm band pass barrier filter. Images of DRAQ5-stained nuclei were acquired using a 635 nm diode laser excitation light, a 635 nm dichroic mirror, and a 655-755 nm band pass barrier filter. Fluorescence images were captured and processed using FV10-ASW 1.6 viewer (Olympus America, Inc.). The cells were scanned in three dimensions as a z-stack of two-dimensional images (1024×1024 pixels). An image cutting horizontally through approximately the middle of the cellular height was selected out of a z-stack of images to differentiate the fluorescence from the polyplexes located in the perinuclear and intranuclear areas.

Statistics

For statistical analysis, triplicate data were analyzed using Analysis Of VAriance (ANOVA) with Bonferroni's multiple comparison test on the significance level of pb0.01 and presented as mean±standard deviation.

Acid-Degradability of Differentially Ketalized PEI

Differentially ketalized PEI at the ratio of 17-96% was synthesized as shown in Scheme 2 of Example 1. Characterization of ketalized PEI using GPC was also shown in Table 2. Hydrolysis of the ketalized low molecular weight PEI (K-LMW PEI) at the endosomal and the physiological pHs was investigated by incubating the polymer in pH 5.0 or pH 7.4 buffer solutions at 37° C. for various periods of time. The disappearance of the ketal linkage peak at 1.2 ppm was quantified by $^1$H-NMR spectroscopy compared with the constant buffer salt peak. The half-lives of $K_{17}$-LMW PEI, $K_{35}$-LMW PEI, $K_{70}$-LMW PEI, and $K_{90}$-LMW PEI (subscript represents the ketalization ratios) at pH 5.0 were calculated to be 2.5, 2.9, 3.8, and 4.6 h, respectively, while their half-lives at pH 7.4 were 26.2, 30.5, 40.8, and 48.1 h, respectively (Table 3). The result showed that the hydrolysis rate of the ketalized PEI was largely dependent on both pH and ketalization ratios. First of all, the hydrolysis of ketalized PEI was observed to be approximately 10 times faster at endosomal pH of 5.0 than at physiological pH of 7.4 regardless of ketalization ratios. This means that acid-degradability was not affected by ketalization ratio. Second, hydrolysis rate tended to decrease with ketalization ratio. This observation can be explained by the following reason. Dimethyl ketal linkage is hydrophobic, and therefore makes ketalized PEI less aqueous soluble. Since hydrolysis of ketal linkage is a proton-mediated catalytic reaction, reduced interactions of the polymers with protons in water lowered the hydrolysis rate of $K_{90}$-LMW PEI than that of $K_{17}$-LMW PEI.

TABLE 2

Characteristics of Ketalized PEI using GPC

| Polymer | Ketalization ratio (%) | $M_n$ | $M_w$ | PDI | Yield[a] (%) |
|---|---|---|---|---|---|
| $K_{17}$-LMW PEI | 17 | 744 | 1027 | 1.38 | 60 |
| K35-LMW PEI | 35 | 1146 | 1444 | 1.26 | 65 |
| $K_{70}$-LMW PEI | 70 | 1485 | 2094 | 1.41 | 71 |
| $K_{90}$-LMW PEI | 90 | 1620 | 2917 | 1.80 | 54 |
| $K_{23}$-HMW PEI | 23 | 18,645 | 32,256 | 1.73 | 59 |
| $K_{37}$-HMW PEI | 37 | 20,266 | 32,425 | 1.60 | 69 |
| $K_{60}$-HMW PEI | 60 | 25,689 | 43,414 | 1.69 | 62 |
| $K_{96}$-HMW PEI | 96 | 34,448 | 63,038 | 1.83 | 60 |

[a]Yield was calculated by dividing the number of moles of ketalized PEI by the number of moles of p-nitrophenyl carbamate-activated PEI. $M_n$ and $M_w$ of 25 kDa HMW PEI and 800 Da LMW PEI (starting materials) were quantified by GPC analysis (HMW PEI: $M_n$ = 15430), $M_w$ = 21754, PDI = 1.41, LMW PEI: $M_n$ = 854, PDI = 1.33).

TABLE 3

Hydrolysis kinetics of various ketalized low molecular weight (k-LMW) PEI at pH 5.0

| | Half lives (h) | |
|---|---|---|
| Polymer | pH 5.0 | pH 7.4 |
| $K_{17}$-LMW PEI | 2.5 | 26.2 |
| $K_{35}$-LMW PEI | 2.9 | 30.5 |
| $K_{70}$-LMW PEI | 3.8 | 40.8 |
| $K_{90}$-LMW PEI | 4.6 | 48.1 |

Effect of Ketalization Ratios on Efficiency of Nucleic Acid Complexation

For efficient endocytosis and transfection in a cell, nucleic acids/polymer polyplexes should be tightly complexed. The effects of different ketalization ratios on nucleic acid complexation in various PEI polyplexes were confirmed by size reduction and ethidium bromide exclusion. As shown in FIG. 10, unketalized high molecular weight (HMW) PEI reduced the size of nucleic acids in the polyplexes with diameters of 80-120 nm above the N/P ratio of 5, while unketalized low molecular weight (LMW) PEI failed to efficiently reduce the size of nucleic acids. $K_{35}$-LMW, $K_{70}$-LMW, and $K_{90}$-LMW PEI polyplexes had slightly larger diameters of 140-200 nm at the N/P ratio of 40 and above than the unketalized HMW PEI polyplexes as shown in FIGS. 10A and B. On the other hand, $K_{17}$-LMW PEI formed largest polyplexes of 230 to 330 nm even at high N/P ratios, indicating its inefficient size reduction. This result indicates that a certain degree of ketalization is minimally required to enhance size reduction efficiency of LMW PEI. The polyplexes prepared by using ketalized high molecular weight PEI (K-HMW PEI) were noticeably larger than the polyplexes prepared by using K-LMW PEI over the observed range of N/P ratios except the ones prepared by using $K_{23}$-HMW PEI polyplexes (FIGS. 10C and D). It seems that ketalization increased condensation efficiency of LMW PEI above the minimal level of 17%, while reduction of nucleic acid size by HMW PEI was hampered by ketalization.

The reduced fluorescence of ethidium bromide intercalated with nucleic acids in various polyplexes was also compared. At the N/P ratio of 40 or above, $K_{35}$-LMW PEI and $K_{70}$-LMW PEI exhibited nucleic acid condensation as efficient as HMW PEI, while $K_{90}$-LMW PEI showed less efficient condensation than $K_{35}$-LMW PEI and $K_{70}$-LMW PEI, but more efficient condensation than $K_{17}$-LMW PEI and unketalized LMW PEI (FIGS. 11A and B). This result indicates that nucleic acid condensation of LMW PEI is enhanced by amino ketal arms in the range of about 35 to about 70%. At the ketalization ratios lower than 35%, both size reduction and ethidium bromide exclusion by K-LMW PEI were inefficient. At the ketalization ratios above 70%, condensation of nucleic acids measured by ethidium bromide exclusion was not efficient, although size reduction of nucleic acids was still efficient. Nucleic acid condensation efficiency by K-HMW PEI measured by ethidium bromide was quite consistent with size reduction of the polyplexes (FIGS. 11C and D). Particularly, nucleic acid condensation efficiency of $K_{96}$-HMW PEI measured by ethidium bromide exclusion was poorer even than that of unketalized LMW PEI. The reason for low condensation efficiency of nucleic acids by K-HMW PEI with higher ketalization ratios can be explained by increased bulky ketal arms conjugated to HMW PEI, which spatially hinders its close interactions with nucleic acids. Generally, siRNA/ketalized PEI polyplexes showed a condensation trend similar to the one of pDNA/ketalized PEI polyplexes (FIGS. 11B and D) regardless of molecular weights of PEI. Again, nucleic acid condensation efficiency of K-LMW PEI was found to be generally proportional to ketalization ratios, although $K_{90}$-LMW PEI showed a slightly higher relative fluorescence value than both $K_{35}$-LMW PEI and $K_{70}$-LMW PEI. Contrarily, nucleic acid condensation efficiency of K-HMW PEI decreased as ketalization ratios increased.

Effect of Ketalization Ratios on DNA Transfection Efficiency

Various polyplexes prepared with eGFP-encoding pDNA and K-LMW or K-HMWPEI at various N/P ratios were used to transfect NIH 3T3 cells. Transfection efficiency was quantified by the relative green fluorescence intensity of the transfected cells. As shown in FIG. 12, for the polyplexes prepared with K-LMWPEI, the optimum N/P ratio of transfection tended to decrease as ketalization ratios increased (i.e., the optimum N/P ratios were 80, 60, and 40 for K-LMWPEI polyplexes with the ketalization ratio of 17, 35, and 70%, respectively) (FIG. 12A). Noticeably, all polyplexes prepared with K-LMW PEI showed enhanced transfection efficiency compared with the ones prepared with unketalized LMW PEI which showed no measurable gene expression. This can be explained since ketalization enhanced nucleic acid complexation by LMW PEI as demonstrated earlier (FIGS. 11 and 12). Transfection efficiency increased with ketalization ratios that were up to 70%, but there was a dramatic decrease in transfection efficiency with the ketalization of 90%, while no difference of the optimum N/P ratios was observed between $K_{70}$-LMW and $K_{90}$-LMW PEI polyplexes. Because both particle size and DNA complexation efficiency of $K_{90}$-LMW PEI polyplexes were not significantly different from those of $K_{70}$-LMW PEI polyplexes, this finding can be explained by a high fraction of ketal linkages which reduce aqueous solubility of the polymer and further interfere cellular uptake. Cytotoxicity tests indicated that high ketalization did not change the levels of cytotoxicity by K-LMW PEI polyplexes regardless of N/P and ketalization ratios.

Unlike the trend shown by K-LMWPEI polyplexes, the optimum N/P ratios of transfection by K-HMW PEI polyplexes increased with ketalization ratios (i.e., the optimum N/P ratios were 20, 40, and 60 for K-HMW PEI polyplexes with the ketalization of 23, 37, and 60%, respectively) (FIG. 12B). Interestingly, ketalization substantially decreased the efficiency of DNA transfection by K-HMW PEI. Only the polyplexes prepared with $K_{23}$-HMW PEI showed substantial gene expression, which might be associated with its relatively efficient DNA complexation compared with the other K-HMW PEI polyplexes (FIGS. 11 and 12). No measurable gene expression was confirmed from the cells incubated with $K_{96}$-HMW PEI polyplexes. Ketalization substantially lowered cytotoxicity of HMW PEI depending on its ketalization ratios. For example, $K_{23}$- and $K_{37}$-HMW PEI polyplexes showed somewhat significant cytotoxicity at high N/P ratios (e.g., N/P ratio of 100 to 140), while $K_{96}$-HMW PEI polyplexes showed almost no cytotoxiticy even at the high N/P ratios. This may be explained by reduced interaction of endogenous nucleic acids with the hydrolyzed PEI whose number of hydroxyl-bearing branches is dependent on ketalization ratios. As known, unketalized HMW PEI showed significant cytotoxicity at high N/P ratios (i.e., N/P ratio of 10 and above), and even an insufficient number of cells were harvested for analysis after being incubated with HMW PEI at the N/P ratio of 60 and above (i.e., no statistically meaningful data points were obtained).

Effect of Different Ketalization Ratios on RNA Interference

Various siRNA/PEI polyplexes were incubated with eGFP-expressing NIH 3T3 cells and reduced gene expression was quantified by mean fluorescence intensity of the cells (FIG. 13). As shown in FIG. 13A, K-LMW PEI polyplexes did not result in any remarkable RNA interference, although some K-LMW PEI polyplexes showed slight eGFP inhibition at the level of 20-37% at high N/P ratios. At high N/P ratios, mildly inhibited gene expression is expected because of relatively high polymer concentrations interfering overall cellular activity. Interestingly, however, K-HMW PEI polyplexes efficiently inhibited expression of eGFP when they were used to deliver anti-eGFP siRNA (FIG. 13B), although KHMW PEI showed decreased nucleic acid complexation capability followed by decreased transfection efficiency (FIGS. 10-12). Unketalized HMWPEI polyplexes showed a significant inhibition of eGFP expression (inhibition degree: 64.0±1.0%) at the N/P ratio of 20, possibly because of their severe cytotoxicity that nonspecifically reduced overall gene expression (FIG. 13B). $K_{23}$-HMW PEI polyplexes reached the maximum suppression of eGFP expression at the N/P ratio of 80 with remarkably reduced cytotoxicity (inhibition degree: 69.7±1.4%) (FIG. 13B). It seems that reduced transfection due to limited nucleic acid complexation capability of $K_{23}$-HMWPEI was offset by enhanced siRNA delivery. Similar to what was observed in DNA transfection (FIG. 12B), efficiency of RNA interference by K-HMW PEI polyplexes decreased with ketalization ratios (FIG. 13B). Significantly reduced cytotoxicity was observed with all ketalized PEI polyplexes regardless of ketalization ratios and molecular weights, while unketalized HMWPEI showed significant cytotoxicity at high N/P ratios (i.e., N/P ratio of 10 and above).

Effect of Ketalization Ratios, Molecular Weights, and Types of Nucleic Acids on Intracellular Localization of Polyplexes Various ketalized and unketalized PEI was complexed with pDNA or siRNA, and the resulting polyplexes were further labeled with Alexa Fluor 488 fluorescence dye. To avoid fluorescence from eGFP, which overlaps with the fluorescence of the dye, firefly luciferase-encoding pDNA was used to form polyplexes. Localization of the various polyplexes was presented by laser scanning confocal microscopy of the middle focal plane which traverses both the cytoplasm and the nucleus of a cell. Only scarce green dots were observed in the cells incubated with $K_{17}$-LMW PEI polyplexes because $K_{17}$-LMW PEI could not efficiently complex nucleic acids (FIGS. 10A and B, and 11A and B), and the resulting polyplexes could not be efficiently internalized. However, a number of the polyplexes prepared with LMW PEI at ketalization of 35% or above were found inside cells. Importantly, a significant number of the $K_{35}$- and $K_{70}$-LMW PEI polyplexes complexing pDNA were localized in the nucleus, but less pDNA/$K_{90}$-LMW PEI polyplexes than the other polyplexes were localized in the nucleus. The ratio of the pDNA/K-LMW PEI polyplexes in the nucleus to the ones in the cytoplasm seems to be corresponding to their transfection efficiency (i.e., higher transfection was observed by $K_{35}$- and $K_{70}$-LMW PEI polyplexes than the one by $K_{90}$-LMW PEI polyplexes) (FIG. 12A). Interestingly, the siRNA-containing K-LMW PEI polyplexes were exclusively localized in the nucleus, except K17-LMW PEI polyplexes which could not efficiently complex the nucleic acids and were found only in the cytoplasm. This finding again parallels the low RNA interference observed with siRNA/K-LMW PEI polyplexes (FIG. 13A) and also implies that nuclear localization of siRNA does not initiate RNA interference because of inaccessibility to the targeting mRNA.

On the other hand, a few of pDNA/$K_{23}$-HMW PEI polyplexes were found in the nucleus, while almost no polyplexes of pDNA/K-HMW PEI at ketalization of 37% or higher were found in the nucleus. A significantly smaller amount of $K_{60}$- and $K_{96}$-HMW PEI polyplexes than $K_{23}$- and $K_{37}$-HMW PEI polyplexes were found in the cells because of their poor pDNA and siRNA complexation capability. This finding explains why only pDNA/K23-HMW PEI polyplexes showed obvious transfection efficiency (FIG. 12B). In comparison to siRNA/K-LMW PEI polyplexes, which were exclusively localized in the nucleus, siRNA/K-HMW PEI polyplexes were mainly distributed in the cytoplasm and resulted in efficient RNA interference (FIG. 13B). Only few siRNA/$K_{96}$-HMW PEI polyplexes were found in the cells because of inefficient nucleic acid complexation (FIGS. 10D and 11D).

Entire peak shift of the fluorescence intensity, rather than split two peaks, was observed with the cells incubated with both pDNA containing and siRNA-containing polyplexes in the histogram of flow cytometry data, implying that the polyplexes delivered pDNA and siRNA to most of the cells with similar intracellular localization of the polyplexes. Fluorescent labeling of polyplexes reduced transfection (about 50%) and gene silencing (about 20%) efficiency compared to unlabeled polyplexes, and there was no significant difference in internalization of various labeled polyplexes. In addition, majority of plasmid DNA and siRNA were found co-localized with the polymers. These results imply that significantly more unlabeled pDNA/PEI polyplexes would have been in the nucleus, and intracellular localization of polyplexes is a determining factor for their biological functions.

The results obtained from nucleic acid complexation, transfection, RNA interference, and intracellular localization of various ketalized PEI polyplexes were compared for elucidating parameters involved in intracellular localization (Table 4). It is clear that ketalization of LMW PEI enhances delivery of pDNA into both the cytoplasm and the nucleus, but exclusively delivers siRNA into the nucleus. On the contrary, ketalization of HMW PEI results in significant localization of both pDNA and siRNA in the cytoplasm. Because selective nuclear and cytoplasmic localizations of pDNA and siRNA, respectively, are required to achieve desired gene expression (transfection) or inhibition (RNA interference) of therapeutic genes, the results demonstrated that this goal can be achieved by precisely tailoring the structures of polymeric nonviral carriers. For example, selective and optimum therapeutic effects can be obtained by utilizing K70-LMW PEI and K23-HMW PEI for transfection and RNA interference, respectively. Finally, as shown in the movies taken only for approximately 30 min, active cell dividing (or mitosis), which results in disappearance of nuclear membrane, was not required for different intracellular localizations of various polyplexes.

TABLE 4

Effects of molecular weights, ketalization ratios, and types of nucleic acids on intracellular localization, transfection, and RNA interference of ketalized PEI

| Nucleic acid/polymer | Condensation | Cystosolic localization | Nuclear localization | Transfection | RNA interference |
|---|---|---|---|---|---|
| pDNA/$K_{17}$-LMW PEI | + | − | − | + | N/A |
| pDNA/$K_{35}$-LMW PEI | +++ | +++ | +++ | +++ | N/A |
| pDNA/$K_{70}$-LMW PEI | +++ | +++ | +++ | +++ | N/A |
| pDNA/K90-LMW PEI | ++ | +++ | ++ | ++ | N/A |
| pDNA/$K_{17}$-LMW PEI | + | − | − | N/A | − |
| pDNA/$K_{35}$-LMW PEI | +++ | − | +++ | N/A | − |
| pDNA/$K_{70}$-LMV PEI | +++ | − | +++ | N/A | − |
| pDNA/$K_{90}$-LMW PEI | + | − | +++ | N/A | + |
| pDNA/$K_{23}$-LMW PEI | +++ | +++ | + | ++ | N/A |
| pDNA/$K_{37}$-LMW PEI | ++ | +++ | − | + | N/A |
| pDNA/$K_{60}$-LMW PEI | ++ | ++ | − | + | N/A |
| pDNA/$K_{96}$-LMW PEI | + | + | − | − | N/A |
| pDNA/$K_{23}$-LMW PEI | +++ | +++ | + | N/A | +++ |
| pDNA/$K_{37}$-LMW PEI | +++ | +++ | − | N/A | ++ |
| pDNA/$K_{60}$-LMW PEI | ++ | ++ | − | N/A | + |
| pDNA/$K_{96}$-LMW PEI | + | + | + | N/A | − |

From the above description of the invention, those skilled in the art will perceive improvements, changes and modifications Such improvements, changes and modifications are within the skill of the art and are intended to be covered by the appended claims. All publications, patents, and patent applications cited in the present application are herein incorporated by reference in their entirety.

Having described the invention, the following is claimed:

1. A complex comprising:
   a nucleic acid and
   a cationic polymer with at least one side chain ionically coupled to the nucleic acid, the at least one side chain including an acid degradable amine-bearing ketal or acetal linkage.

2. The complex of claim 1, the cationic polymer being a polyamine.

3. The complex of claim 2, the polyamine being a polyethyleneimine.

4. The complex of claim 1, the at least one side chain including a ketal group or acetal group having the following general formula:

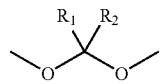

wherein $R_1$ and $R_2$ are each individually selected from the group consisting of H, an alkyl, a substituted alkyl.

5. The complex of claim 1, the at least one side chain having the following general formula:

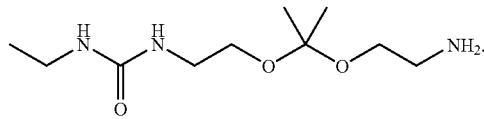

6. The complex of claim 3, the polyethyleneimine having a molecular weight of about 400 to about 1200 daltons.

7. The complex of claim 6, the nucleic acid comprising DNA.

8. The complex of claim 3, the polyethyleneimine having a molecular weight of about 20 to about 30 kilodaltons.

9. The complex of claim 8, the nucleic acid comprising at least one of si RNA or microRNA.

10. The complex of claim 3, the molar ratio of nitrogen atoms in the polyethyleneimine to phosphate atoms in the nucleic acid (N/P ratio) being about 25 to about 100.

11. The complex of claim 3, having a ketalization ratio of about 35% to about 70%.

12. A complex comprising:
    a nucleic acid and a polyethyleneimine with a side chain ionically coupled to the nucleic acid, the polyethyleneimine including a repeating unit with the following general formula:

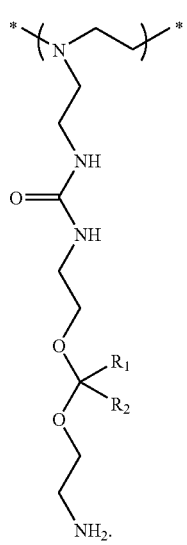

13. The complex of claim 12, the polyethyleneimine having a molecular weight of about 400 to about 1200 daltons.

14. The complex of claim 13, the nucleic acid comprising DNA.

15. The complex of claim 12, the polyethyleneimine having a molecular weight of about 20 to about 30 kilodaltons.

16. The complex of claim 15, the nucleic acid comprising at least one of siRNA or microRNA.

17. The complex of claim 12, the molar ratio of nitrogen atoms in the polyethyleneimine to phosphate atoms in the nucleic acid (N/P ratio) being about 40 to about 80 and having a ketalization ratio of about 35% to about 70%.

* * * * *